US012770801B2

(12) United States Patent
Dinca et al.

(10) Patent No.: US 12,770,801 B2
(45) Date of Patent: Oct. 20, 2026

(54) FUSED AROMATIC MOLECULES AS ELECTRODE MATERIALS

(71) Applicant: Massachusetts Institute of Technology, Cambridge, MA (US)

(72) Inventors: Mircea Dinca, Belmont, MA (US); Harish Banda, Cambridge, MA (US); Tianyang Chen, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 291 days.

(21) Appl. No.: 18/684,127

(22) PCT Filed: Jan. 26, 2022

(86) PCT No.: PCT/US2022/013925
§ 371 (c)(1),
(2) Date: Feb. 15, 2024

(87) PCT Pub. No.: WO2023/022750
PCT Pub. Date: Feb. 23, 2023

(65) Prior Publication Data

US 2025/0140486 A1 May 1, 2025

Related U.S. Application Data

(60) Provisional application No. 63/234,849, filed on Aug. 19, 2021.

(51) Int. Cl.
*H01G 11/58* (2013.01)
*C07D 241/46* (2006.01)
(Continued)

(52) U.S. Cl.
CPC ........... *H01G 11/58* (2013.01); *C07D 241/46* (2013.01); *H01G 11/48* (2013.01); *H01M 4/60* (2013.01)

(58) Field of Classification Search
CPC ........ H01G 11/58; H01G 11/48; H01G 11/02; H01G 11/30; C07D 241/46; H01M 4/60;
(Continued)

(56) References Cited

U.S. PATENT DOCUMENTS 2,611,772 A 9/1952 Allen et al.
4,233,215 A 11/1980 Driscoll et al.
(Continued)

FOREIGN PATENT DOCUMENTS

CA 3115290 A1 * 4/2020 ............. H01B 1/121
CA 3160705 A1 * 6/2021 ............. H01G 11/38
(Continued)

OTHER PUBLICATIONS

WO '246 translation (Year: 2020).*
(Continued)

*Primary Examiner* — Dion R. Ferguson
(74) *Attorney, Agent, or Firm* — Wolf, Greenfield & Sacks, P.C.

(57) ABSTRACT

Compositions comprising fused aromatic systems and associated electrodes, electrochemical cells, and charge storage devices are generally described. Preferably, the aromatic comprising a bis-tetraamino-benzoquinone molecule and/or a tautomer, oligomer, and/or polymer thereof. Alternatively, the aromatic composition comprises an active material comprising a fused aromatic system comprising carbon atoms, hydrogen atoms, and a plurality of heteroatoms each replacing a carbon atom.

19 Claims, 17 Drawing Sheets

(51) Int. Cl.
*H01G 11/48* (2013.01)
*H01M 4/60* (2006.01)

(58) Field of Classification Search
CPC ............... H01M 4/608; H01M 10/052; H01M 10/0566; C08G 73/06; C08G 73/0694; Y02E 60/10; Y02E 60/13
See application file for complete search history.

(56) References Cited

U.S. PATENT DOCUMENTS

| | | | | |
|---|---|---|---|---|
| 4,581,349 | A | 4/1986 | Wright et al. | |
| 6,743,877 | B1 | 6/2004 | Armand et al. | |
| 9,770,709 | B2 | 9/2017 | Swager et al. | |
| 2003/0118877 | A1 | 6/2003 | Armand et al. | |
| 2007/0108438 | A1* | 5/2007 | Lindsey | B82Y 30/00 257/40 |
| 2010/0204407 | A1* | 8/2010 | Bouquet | C08F 4/56 526/89 |
| 2014/0087255 | A1 | 3/2014 | Kim et al. | |
| 2016/0336622 | A1 | 11/2016 | Zhang | |
| 2023/0077307 | A1 | 3/2023 | Oono et al. | |
| 2025/0140486 | A1* | 5/2025 | Dinca | C08G 73/06 |
| 2026/0100367 | A1 | 4/2026 | Dinca et al. | |

FOREIGN PATENT DOCUMENTS

| | | | | | |
|---|---|---|---|---|---|
| CN | 114204020 | A | | 3/2022 | |
| CN | 115505122 | A | | 12/2022 | |
| CN | 116355230 | B | | 4/2024 | |
| CN | 118812847 | B | | 12/2024 | |
| CN | 119977895 | B | | 7/2025 | |
| CN | 120230286 | B | | 8/2025 | |
| EP | 4345968 | A1 | | 4/2024 | |
| JP | 2002-298844 | A | | 10/2002 | |
| JP | 2010-195791 | A | | 9/2010 | |
| JP | 2014-505580 | A | | 3/2014 | |
| JP | 2020066681 | A | * | 4/2020 | H01M 4/1399 |
| WO | WO-2020037246 | A1 | * | 2/2020 | C08G 65/48 |
| WO | WO 2020/084828 | A1 | | 4/2020 | |
| WO | WO-2022235931 | A1 | * | 11/2022 | H01M 10/056 |
| WO | WO 2023/022750 | A1 | | 2/2023 | |
| WO | WO 2024/072426 | A1 | | 4/2024 | |

OTHER PUBLICATIONS

Extended European Search Report for EP Application No. 25191247.3 dated Jan. 9, 2026.
Vitaku et al., Phenazine-Based Covalent Organic Framework Cathode Materials with High Energy and Power Densities. JACS. Dec. 10, 2019;142(1):16-20. doi: 10.1021/jacs.9b08147.
U.S. Appl. No. 19/114,743, filed Mar. 24, 2025, Dinca et al.
EP 22711141.6, Feb. 16, 2024, Partial European Search Report.
EP 22711141.6, May 8, 2024, Extended European Search Report.
PCT/US2022/013925, Apr. 19, 2022, Invitation to Pay Additional Fees.
PCT/US2022/013925, Jun. 30, 2022, International Search Report and Written Opinion.
PCT/US2022/013925, Feb. 29, 2024, International Preliminary Report on Patentability.
EP 22203788.9, Apr. 8, 2024, Extended European Search Report.
PCT/US2022/047389, Jan. 3, 2023, Invitation to Pay Additional Fees.
PCT/US2022/047389, Mar. 22, 2023, International Search Report and Written Opinion.
PCT/US2022/047389, Apr. 10, 2025, International Preliminary Report on Patentability.
Partial European Search Report for Application No. 22711141.6, mailed Feb. 16, 2024.
Extended European Search Report for Application No. 22711141.6, mailed May 8, 2024.
Invitation to Pay Additional Fees for Application No. PCT/US2022/013925, mailed Apr. 19, 2022.
International Search Report and Written Opinion for Application No. PCT/US2022/013925, mailed Jun. 30, 2022.
International Preliminary Report on Patentability for Application No. PCT/US2022/013925, mailed Feb. 29, 2024.
Extended European Search Report for Application No. 22203788.9, mailed Apr. 8, 2024.
Invitation to Pay Additional Fees for Application No. PCT/US2022/047839, mailed Jan. 3, 2023.
International Search Report and Written Opinion for Application No. PCT/US2022/047839, mailed Mar. 22, 2023.
International Preliminary Report on Patentability for Application No. PCT/US2022/047839, mailed Apr. 10, 2025.
Alt et al., Investigation into the use of quinone compounds—for battery cathodes. Electrochimica Acta. May 1972;17(5):873-87.
Audi et al., Extendable nickel complex tapes that reach NIR absorptions. Chem Commun (Camb). Dec. 14, 2014;50(96):15140-3. doi: 10.1039/c4cc07353c.
Augustyn et al., High-rate electrochemical energy storage through Li+ intercalation pseudocapacitance. Nat Mater. Jun. 2013;12(6):518-22. doi: 10.1038/nmat3601. Epub Apr. 14, 2013.
Banda et al., Dual-Ion Intercalation and High Volumetric Capacitance in a Two-Dimensional Non-Porous Coordination Polymer. Angew Chem Int Ed Engl. Dec. 20, 2021;60(52):27119-27125. doi: 10.1002/anie.202112811. Epub Nov. 18, 2021.
Banda et al., High-Capacitance Pseudocapacitors from Li+ Ion Intercalation in Nonporous, Electrically Conductive 2D Coordination Polymers. J Am Chem Soc. Feb. 10, 2021;143(5):2285-2292. doi: 10.1021/jacs.0c10849. Epub Feb. 1, 2021.
Burke et al., The oxygen electrode. Part 8.—Oxygen evolution at ruthenium dioxide anodes. J Chem Soc Faraday Trans. 1977;73:1659-71. doi: 10.1039/F19777301659.
Chao et al., Toward High-Voltage Aqueous Batteries: Super- or Low-Concentrated Electrolyte? Joule. Sep. 2020;4(9):1846-1851. doi: 10.1016/j.joule.2020.07.023.
Chen et al., Capacitive conjugated ladder polymers for fast-charge and -discharge sodium-ion batteries and hybrid supercapacitors. J Mater Chem A. 2019;7(36):20891-20898. doi: 10.1039/C9TA07546A.
Chen et al., High-rate, high-capacity electrochemical energy storage in hydrogen-bonded fused aromatics. ChemRxiv. Jan. 31, 2022. doi: 10.26434/chemrxiv-2022-brq5c, https://chemrxiv.org/engage/chemrxiv/article-details/61f301954b950018140c5d8e, 23 pages.
Cheung, New Energy Outlook 2021. BloombergNEF. Nov. 8, 2021.
Choi et al., Achieving high energy density and high power density with pseudocapacitive materials. Nat Rev Mater. Oct. 1, 2019;5:5-19. doi: 10.1038/s41578-019-0142-z.
Eftekhari et al., Polyaniline supercapacitors. J of Pow Sources. Apr. 15, 2017; 347:86-107. doi: 10.1016/j.jpowsour.2017.02.054.
Fleischmann et al., Pseudocapacitance: From Fundamental Understanding to High Power Energy Storage Materials. Chem Rev. Jul. 22, 2020;120(14):6738-6782. doi: 10.1021/acs.chemrev.0c00170. Epub Jun. 28, 2020.
Guo et al., An Environmentally Friendly and Flexible Aqueous Zinc Battery Using an Organic Cathode. Angew Chem Int Ed Engl. Sep. 3, 2018;57(36):11737-11741. doi: 10.1002/anie.201807121. Epub Aug. 2, 2018.
Han et al., Proton-assisted calcium-ion storage in aromatic organic molecular crystal with coplanar stacked structure. Nat Commun. Apr. 23, 2021;12(1):2400. doi: 10.1038/s41467-021-22698-9.
Isono et al., Hydrogen bond-promoted metallic state in a purely organic single-component conductor under pressure. Nat Commun. 2013;4:1344. doi: 10.1038/ncomms2352.
Jaumaux et al., Localized Water-In-Salt Electrolyte for Aqueous Lithium-Ion Batteries. Angew Chem Int Ed Engl. Sep. 1, 2021;60(36):19965-19973. doi: 10.1002/anie.202107389. Epub Jul. 26, 2021.
Koshika et al., An Aqueous, Electrolyte-Type, Rechargeable Device Utilizing a Hydrophilic Radical Polymer-Cathode. Macromol. Chem. Phys. 2009;210:1989-95.
Lee et al., Fully conjugated ladder polymers. Chem Sci. Apr. 1, 2017;8(4):2503-2521. doi: 10.1039/c7sc00154a. Epub Feb. 17, 2017.

(56) References Cited

OTHER PUBLICATIONS

Li et al., A general Lewis acidic etching route for preparing MXenes with enhanced electrochemical performance in non-aqueous electrolyte. Nat Mater. Aug. 2020; 19(8):894-899. doi: 10.1038/s41563-020-0657-0. Epub Apr. 13, 2020. Erratum in: Nat Mater. Apr. 2021;20(4):571. doi: 10.1038/s41563-021-00925-4.
Li et al., A Small Molecular Symmetric All-Organic Lithium-Ion Battery. Angew Chem Int Ed Engl. Aug. 15, 2022;61(33):e202207221. doi: 10.1002/anie.202207221. Epub Jul. 7, 2022.
Li et al., High-Nickel NMA: A Cobalt-Free Alternative to NMC and NCA Cathodes for Lithium-Ion Batteries. Adv Mater. Aug. 2020;32(33):e2002718. doi: 10.1002/adma.202002718. Epub Jul. 6, 2020.
Liang et al., Universal quinone electrodes for long cycle life aqueous rechargeable batteries. Nat Mater. Aug. 2017;16(8):841-848. doi: 10.1038/nmat4919. Epub Jun. 19, 2017.
Lin et al., A high capacity small molecule quinone cathode for rechargeable aqueous zinc-organic batteries. Nat Commun. Jul. 20, 2021;12(1):4424. doi: 10.1038/s41467-021-24701-9.
Lu et al., Design Strategies toward Enhancing the Performance of Organic Electrode Materials in Metal-Ion Batteries. Chem. Dec. 2018;4(12):2786-2813. doi: 10.1016/j.chempr.2018.09.005.
Ma et al., Disassembly-Reassembly Approach to RuO2 /Graphene Composites for Ultrahigh Volumetric Capacitance Supercapacitor. Small. Aug. 2017;13(30). doi: 10.1002/smll.201701026. Epub Jun. 26, 2017.
Mathis et al., Energy Storage Data Reporting in Perspective—Guidelines for Interpreting the Performance of Electrochemical Energy Storage Systems. Adv Energy Mater. Sep. 2019;9(39):1902007. doi: 10.1002/aenm.201902007.
Melin et al., Global implications of the EU battery regulation. Science. Jul. 23, 2021;373(6553):384-387. doi: 10.1126/science.abh1416.
Nam et al., Redox-Active Phenanthrenequinone Triangles in Aqueous Rechargeable Zinc Batteries. J Am Chem Soc. Feb. 5, 2020;142(5):2541-2548. doi: 10.1021/jacs.9b12436. Epub Jan. 21, 2020.
Ortiz et al., Gigafactories: Europe's major commitment to economic recovery through the development of battery factories. CIC Energi Gune. Apr. 7, 2021. https://cicenergigune.com/en/blog/gigafactories-europe-commitment-economic-recovery-battery-factories [last accessed Apr. 25, 2025] 3 pages.
Poizot et al., Opportunities and Challenges for Organic Electrodes in Electrochemical Energy Storage. Chem Rev. Jul. 22, 2020;120(14):6490-6557. doi: 10.1021/acs.chemrev.9b00482. Epub Mar. 24, 2020.
Russell et al., High-performance organic pseudocapacitors via molecular contortion. Nat Mater. Aug. 2021;20(8):1136-1141. doi: 10.1038/s41563-021-00954-z. Epub Apr. 1, 2021.
Sato et al., Electronic and crystal structures of 1,2,3-triazole-fused p-benzoquinone derivatives. CrystEngComm. 2017;19(6):910-7. Epub Dec. 5, 2016.
Sheberla et al., Conductive MOF electrodes for stable supercapacitors with high areal capacitance. Nat Mater. Feb. 2017;16(2):220-224. doi: 10.1038/nmat4766. Epub Oct. 10, 2016.
Sheberla et al., High electrical conductivity in $Ni_3$(2,3,6,7,10,11-hexaiminotriphenylene)$_2$, a semiconducting metal-organic graphene analogue. J Am Chem Soc. Jun. 25, 2014;136(25):8859-62. doi: 10.1021/ja502765n. Epub Apr. 25, 2014.
Shi et al., High Active Material Loading in All-Solid-State Battery Electrode via Particle Size Optimization. Advanced Energy Materials. Jan. 7, 2020;10(1):1902881. Epub Dec. 3, 2019.
Simon et al., Materials for electrochemical capacitors. Nat Mater. Nov. 2008;7(11):845-54. doi: 10.1038/nmat2297.
Simon et al., Materials science. Where do batteries end and supercapacitors begin? Science. Mar. 14, 2014;343(6176):1210-1. doi: 10.1126/science.1249625.
Simon et al., Perspectives for electrochemical capacitors and related devices. Nat Mater. Nov. 2020;19(11):1151-1163. doi: 10.1038/s41563-020-0747-z. Epub Aug. 3, 2020.
Suo et al., "Water-in-salt" electrolyte enables high-voltage aqueous lithium-ion chemistries. Science. Nov. 20, 2015;350(6263):938-43. doi: 10.1126/science.aab1595. Erratum in: Science. Dec. 11, 2015;350(6266):aad9367. doi: 10.1126/science.aad9367.
Tang et al., Tailoring π-Conjugated Systems: From π-π Stacking to High-Rate-Performance Organic Cathodes. Chem. Nov. 2018;4(11):2600-2614. doi: 10.1016/j.chempr.2018.08.014.
Trasatti et al., Ruthenium dioxide: A new interesting electrode material. Solid state structure and electrochemical behaviour. J Electroanalytical Chem and Interfacial Electrochemistry . Feb. 1971;29(2):A1-A5. doi: 10.1016/S0022-0728(71)80111-0.
Vitaku et al., Phenazine-Based Covalent Organic Framework Cathode Materials with High Energy and Power Densities. ChemRxiv. Jul. 31, 2019. doi: 10.26434/chemrxiv.9185948.v1.
Wang et al., A Selectively Permeable Membrane for Enhancing Cyclability of Organic Sodium-Ion Batteries. Adv Mater. Nov. 2016;28(41):9182-9187. doi: 10.1002/adma.201603240. Epub Aug. 29, 2016. Author manuscript, 16 pages.
Wang et al., Binding Zinc Ions by Carboxyl Groups from Adjacent Molecules toward Long-Life Aqueous Zinc-Organic Batteries. Adv Mater. Apr. 2020;32(16):e2000338. doi: 10.1002/adma.202000338. Epub Mar. 5, 2020.
Wang et al., Pseudocapacitive Contributions to Electrochemical Energy Storage in TIO2 (Anatase) Nanoparticles. J Phys Chem C. 2007;111(40):14925-14931. doi:10.1021/jp074464w.
Wen et al., The role of cations of the electrolyte for the pseudocapacitive behavior of metal oxide electrodes, $MnO_2$ and $RuO_2$. Electrochim Acta. Nov. 30, 2004;50(2-3):849-855. doi: 10.1016/j.electacta.2004.02.056.
Wu et al., Diffusion-free Grotthuss topochemistry for high-rate and long-life proton batteries. Nat Energy. Feb. 2019;4(2):123-130. doi:10.1038/s41560-018-0309-7.
Xu et al., Branched conjugated polymers for fast capacitive storage of sodium ions. J Mater Chem A. 2020;8(45):23851-23856. doi: 10.1039/DOTA07658A.
Yang et al., Alkaline Benzoquinone Aqueous Flow Battery for Large-Scale Storage of Electrical Energy. Advanced Energy Materials. Mar. 15, 2018;8(8):1702056. Epub Dec. 4, 2017.
Zhao et al., High-capacity aqueous zinc batteries using sustainable quinone electrodes. Sci Adv. Mar. 2, 2018;4(3):eaao1761. doi: 10.1126/sciadv.aao1761.
Zheng et al., Hydrous Ruthenium Oxide as an Electrode Material for Electrochemical Capacitors. J Electrochem Soc. 1995:142:2699. doi: 10.1149/1.2050077.
Office Action for JP Application No. 2024-509465 dated Dec. 26, 2025.
Shi et al., Nitrogen-rich covalent organic frameworks with multiple carbonyls for high-performance sodium batteries. Nat Commun. Jan. 10, 2020;11(1):178. doi: 10.1038/s41467-019-13739-5.
International Search Report and Written Opinion for Application No. PCT/US2024/022179, mailed Jun. 10, 2024.
Invitation to Pay Additional Fees for Application No. PCT/US2025/021954, mailed May 15, 2025.
International Search Report and Written Opinion for Application No. PCT/US2025/021954, mailed Aug. 6, 2025.
Extended European Search Report for Application No. 24167910.9, mailed Nov. 14, 2024.
Extended European Search Report for Application No. 25167185.5, mailed Sep. 11, 2025.
Chen et al., A Layered Organic Cathode for High-Energy, Fast-Charging, and Long-Lasting Li-Ion Batteries. ACS Cent Sci. Jan. 18, 2024;10(3):569-578. doi: 10.1021/acscentsci.3c01478.
Chen et al., High-rate, high-capacity electrochemical energy storage in hydrogen-bonded fused aromatics. Joule. May 17, 2023;7:986-1002.
Peng et al., Constructing Carbon Nanotube-Enhanced Ultra-Thin Organic Compounds with Multi-Redox Sites for "All-Temperature" Potassium-Ion Battery Anode and its Step-Wise K-Storage Mechanism. Small. May 2024;20(20):e2308953. doi: 10.1002/smll.202308953. Epub Dec. 10, 2023.
Partial European Search Report for Application No. 25191247.3, mailed Oct. 16, 2025.

(56) References Cited

OTHER PUBLICATIONS

Tuttle et al., Synergistic Effect of Hydrogen Bonding and π-π Stacking Enables Long Cycle Life in Organic Electrode Materials. ACS Energy Letters. Jan. 25, 2021;6(2):643-9.
Office Action for EP Application No. 22711141.6 dated Apr. 30, 2026.
Office Action for KR Application No. 10-2024-7008576 dated Apr. 23, 2026.
Office Action for CN Application No. 202280053699.0 dated May 29, 2026.
Office Action for JP Application No. 2025-517957 dated Jun. 16, 2026.
Litterio et al., Comparison of the Structure of Advanced Organic Electrode Materials, TAPT and "TAQ", by Multinuclear NMR and Stability Analysis. J Phys Chem A. Jul. 17, 2026. doi: 10.1021/acs.jpca.6c03213. Epub ahead of print.

* cited by examiner

FUSED AROMATIC MOLECULES AS ELECTRODE MATERIALS

RELATED APPLICATIONS

This application is a national stage filing under 35 U.S.C. § 371 of International Patent Application No. PCT/US2022/013925, filed Jan. 26, 2022, and entitled "FUSED AROMATIC MOLECULES AS ELECTRODE MATERIALS," which claims priority to U.S. Provisional Application No. 63/234,849, filed Aug. 19, 2021, and entitled "FUSED AROMATIC MOLECULES AS ELECTRODE MATERIALS," each of which is incorporated herein by reference in its entirety for all purposes.

TECHNICAL FIELD

Compositions comprising fused aromatic systems and associated electrodes, electrochemical cells, and charge storage devices are generally described.

BACKGROUND

Supercapacitors (SCs) are energy storage devices that offer high power densities and long-term cycling stability compared to lithium-ion batteries (LIBs). The energy density of a typical SC that uses porous carbon as an electrode material, however, is two orders of magnitude lower than LIBs. Bridging this gap in energy densities while maintaining high power of SCs is a challenge toward fabricating an ideal storage device. One strategy to bridge the gap in energy densities is to use pseudocapacitive electrode materials. Inorganic oxides, for example, may undergo rapid faradaic processes and deliver charge storage (~160 mAh/g) comparable to batteries, while functioning on a faster time scale of seconds. The best performing inorganic oxides (e.g., hydrous noble metal oxides such as $RuO_2·xH2O$ and $IrO_2·xH2O$), however, are prohibitively expensive for commercial use in SCs.

SUMMARY

Compositions comprising fused aromatic systems and associated electrodes, electrochemical cells, and charge storage devices are generally described. The subject matter of the present invention involves, in some cases, interrelated products, alternative solutions to a particular problem, and/or a plurality of different uses of one or more systems and/or articles.

According to some embodiments, a composition is described, the composition comprising a bis-tetraamino-benzoquinone molecule of the structure:

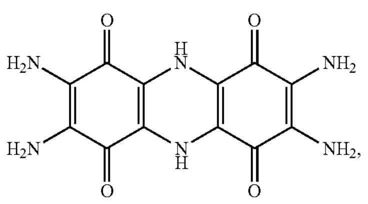 [SMILES: Nc1c(N)c(=O)c2[nH]c3c(=O)c(N)c(N)c(=O)c3[nH]c2c1=O]

and/or a tautomer, oligomer, and/or polymer thereof.

According to certain embodiments, an electrode is described, the electrode comprising a bis-tetraamino-benzoquinone molecule of the structure:

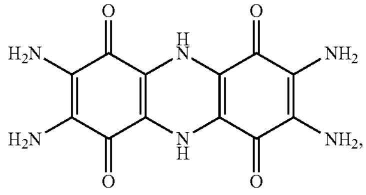 [SMILES: Nc1c(N)c(=O)c2[nH]c3c(=O)c(N)c(N)c(=O)c3[nH]c2c1=O]

and/or a tautomer, oligomer, and/or polymer thereof.

According to some embodiments, an electrochemical cell is described, the electrochemical cell comprising a first electrode, a second electrode, and an electrolyte, wherein the first electrode and/or second electrode is an electrode as described above, e.g., comprising a bis-tetraamino-benzoquinone molecule of the structure:

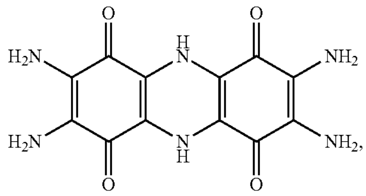 [SMILES: Nc1c(N)c(=O)c2[nH]c3c(=O)c(N)c(N)c(=O)c3[nH]c2c1=O]

and/or a tautomer, oligomer, and/or polymer thereof.

According to certain embodiments, an electrochemically active charge storage material is described, the electrochemically active charge storage material comprising an active material comprising a fused aromatic system comprising carbon atoms, hydrogen atoms, and a plurality of heteroatoms each replacing a carbon atom, wherein the ratio of carbon atoms to heteroatoms is between greater than 1 and less than 2, wherein the plurality of heteroatoms comprise N, O, S, and/or Se.

According to some embodiments, an electrochemically active charge storage material is described, the electrochemically active charge storage material comprising an active material comprising a fused aromatic system comprising carbon atoms, hydrogen atoms, and a plurality of heteroatoms each replacing a carbon atom, wherein at least a portion of the fused aromatic system is in a planar and/or two-dimensional configuration via a number hydrogen-bonding interactions, wherein the number of hydrogen-bonding interactions is between greater than or equal to 0.3 and less than or equal to 1 hydrogen-bonds per mole of carbon atoms.

According to certain embodiments, a charge storage device is described, the charge storage device comprising an electrochemically active charge storage material comprising an active material, wherein the active material comprises a fused aromatic system comprising carbon, hydrogen, and one or more heteroatoms replacing a carbon atom, wherein the electrochemically active charge storage material has a charge capacity of greater than or equal to 100 mAh per gram of active material, and/or the electrochemically active charge storage material has a charge capacity of greater than or equal to 50 mAh per gram of electrochemically active charge storage material.

According to some embodiments, a charge storage device is described, the charge storage device comprising an electrochemically active charge storage material comprising an active material, wherein the active material comprises a fused aromatic system comprising carbon, hydrogen, and one or more heteroatoms replacing a carbon atom, wherein the electrochemically active charge storage material is disposed in an electrolyte, and the electrochemically active charge storage material has a charge capacity that is at least 50% greater when the pH value of the electrolyte is between greater than or equal to 0 and less than or equal to 2 or between greater than or equal to 12 and less than or equal to 15 as compared to when the pH value of the electrolyte is between greater than 2 and less than 12.

According to certain embodiments, a charge storage device is described, the charge storage device comprising an electrochemically active charge storage material comprising an active material, wherein the active material comprises a fused aromatic system comprising carbon, hydrogen, and one or more heteroatoms replacing a carbon atom, wherein, the electrochemically active charge storage material delivers at least 90% of its charge capacity at a voltage higher than 2.0 V vs. $Li^+/Li$ standard reference electrode.

According to some embodiments, a charge storage device is described, the charge storage device comprising an electrochemically active charge storage material comprising an active material, wherein the active material comprises a fused aromatic system comprising carbon atoms, hydrogen atoms, and a plurality of heteroatoms each replacing a carbon atom, wherein a ratio of moles of electrons stored as charge per mole of heteroatoms is between greater than or equal to 0.3 and less than or equal to 0.6.

According to certain embodiments, a charge storage device is described, the charge storage device comprising an electrochemically active charge storage material comprising an active material, wherein the active material comprises an organic material, wherein the active material has a solubility at ambient temperature and pressure of less than or equal to 1 millimoles per liter of solvent, and the electrochemically active charge storage material has greater than or equal to 85% charge capacity retention after at least 20,000 cycles.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
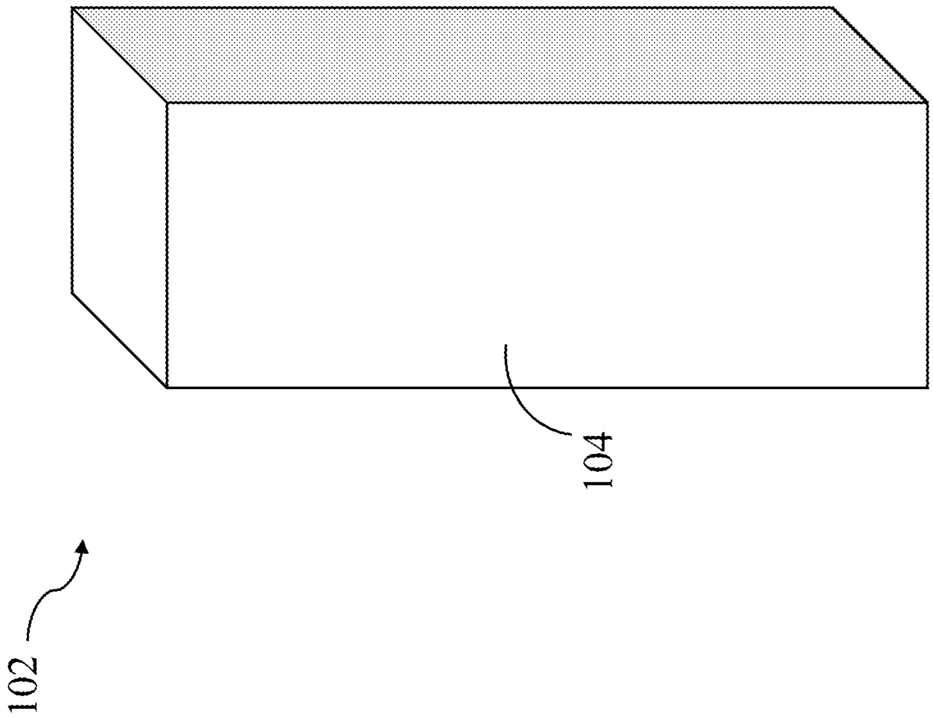
FIG. 1 shows, according to certain embodiments, a schematic diagram of an electrode.

Growing demand for electrification of transportation sector and decarbonization of grid requires development of electrochemical energy storage (EES) systems that cater to various energy and power needs. As the state-of-the-art EES devices, conventional lithium-ion cells (LICs) and electrochemical capacitors (ECs) typically offer either high energy or high power. Several attempts have aimed at achieving high power and energy densities in a hybrid energy storage system (HESS) by integrating LICs and ECs at the device level. This approach represents a modular way of supplying high energy and power to applications, where power demands vary with time or the possibility to recover energy at high power is as important as power delivery. The complexity and costs involved in such device integration, however, precludes use in package sensitive applications such as in electric vehicles. The Inventors have realized that there is a strong interest in developing materials that combine high charge capacity of LICs with fast charging and long cycling life of ECs in a single EES device.

Electrode materials possessing abundant redox-active sites may be suitable as high capacity and high power materials, as the redox-sites rapidly transport electric and ionic charges throughout the electrode bulk. Such a charge-storage mechanism, typically known as pseudocapacitance, has primarily been identified in thin films of redox-active transition metal oxides, nitrides, and carbides with short charge diffusion lengths. Thick electrode films of these materials with practically-relevant mass loadings, however, deliver sub-optimal performances due to poor bulk ion and electron transport. Moreover, the convoluted roles of surface chemistry, crystallinity, and degree of hydration in the electrochemical behaviors of conventional inorganic materials restricts a precise design control and instead requires composite synthesis and nano-engineering.

In contrast to the conventional inorganic materials described above, organic materials offer great structural tunability and synthetic feasibility for diverse designs of electrode materials that utilize earth-abundant elements. However, due to their poor intrinsic electrical conductivity, limited electronic delocalization, and high solubility in electrolytes, conventional organic molecules deliver inferior electrochemical performances compared to their inorganic counterparts. Although strategies such as polymerization and compositing organic molecules using insoluble substrates can limit electrode dissolution, molecular designs that simultaneously enhance the charge transport and storage in insoluble organic solids are strongly desired.

The Inventors have realized and appreciated that fused aromatic materials, for example those comprising bis-tetraaminobenzoquinone (BTABQ) and oligomers and/or polymers thereof, may used as electrode active materials and are suitable for EES. The fused aromatic materials possess dense redox-active sites in the aromatic backbone with extended conjugation. In some embodiments, for example, the carbon to heteroatom (e.g., N, O) ratio of the material is less than 1.3. The materials form insoluble solids in both organic and aqueous media through strong intermolecular hydrogen bonding and donor-acceptor π-π interactions. Fused aromatic material, such as those comprising BTABQ and oligomers and/or polymers thereof, exhibit excellent charge-storage capacities at high charge-discharge rates in various electrolytes, primarily originating from rapid pseudocapacitive intercalation processes throughout the electrode bulk due to electronic delocalization and facile ion transport. The electronic delocalization and facile ion transport is facilitated by a dense presence of redox-active groups and an alternating arrangement of electron donor and electron acceptor aromatic rings in the fused aromatic material.

According to certain embodiments, a composition is described. The composition comprises, in some embodiments, an organic material. In certain embodiments, for example, the composition comprises a fused aromatic system. As used herein, the term "fused aromatic system" is given its ordinary meaning in the art and generally refers to two or more cyclic (e.g., monocyclic, bicyclic, tricyclic, etc.) aromatic rings that share connecting bonds, and/or a plurality of two or more cyclic (e.g., monocyclic, bicyclic, tricyclic, etc.) aromatic rings that share connecting bonds. In some embodiments, for example, the fused aromatic system may comprise one or more fused aromatic molecules comprising at least two aromatic rings that share connecting bonds. As would generally be understood by a person of ordinary skill in the art, the fused aromatic system may be an extended conjugation system that advantageously facilitates electronic charge delocalization and diffusion of ionic charges.

The fused aromatic system may comprise carbon atoms and hydrogen atoms, as would generally be understood by a person of ordinary skill in the art. In certain embodiments, the fused aromatic system may comprise one or more heteroatoms replacing a carbon atom. Examples of suitable heteroatoms include, for example, nitrogen (N), oxygen (O), sulfur(S), and/or selenium (Se).

According to certain embodiments, the fused aromatic system may have any of a variety of suitable ratios of carbon atoms to heteroatoms (e.g., N, O, S, and/or Se). A relatively low ratio of carbon atoms to heteroatoms (e.g., less than 2) advantageously provides a system with more redox-active sites as compared to a system with a high ratio of carbon atoms to heteroatoms (e.g., greater than 2) but is otherwise equivalent, thereby providing sufficient transport pathways for electric and/or ionic charges through the bulk of the material. In certain embodiments, for example, the fused aromatic system may comprise a relatively high number of redox-active sites, including, but not limited to, carbonyl groups, amine groups, and/or imine groups. The presence of heteroatoms in the fused aromatic system may also advantageously provide an alternating arrangement of electron donor and electron acceptor aromatic rings, therefore facilitating the transport of electric and/or ionic charges through the bulk of the material.

In some embodiments, the ratio of carbon atoms to heteroatoms in the fused aromatic system is greater than 1, greater than or equal to 1.1, greater than or equal to 1.2, greater than or equal to 1.3, greater than or equal to 1.4, greater than or equal to 1.5, greater than or equal to 1.6, greater than or equal to 1.7, greater than or equal to 1.8, or greater than or equal to 1.9. In certain embodiments, the ratio of carbon atoms to heteroatoms in the fused aromatic system is less than 2, less than or equal or equal to 1.9, less than or equal to 1.8, less than or equal to 1.7, less than or equal to 1.6, less than or equal to 1.5, less than or equal to 1.4, less than or equal to 1.2, or less than or equal to 1.1. Combinations of the above recited ranges are also possible (e.g., the ratio of carbon atoms to heteroatoms in the fused aromatic system is between greater than 1 and less than 2, the ratio of carbon atoms to heteroatoms in the fused aromatic system is between greater than 1.2 and less than 1.4). Other ranges are also possible.

In certain embodiments, at least a portion of the fused aromatic system may be interconnected via one or more hydrogen-bonding interactions. In some embodiments, for example, at least a portion of BTABQ molecules, oligomers, and/or polymers thereof may interact with each other in a planar and/or two-dimensional configuration via hydrogen-bonding. According to some embodiments, the hydrogen-bonding interactions may be between one or more hydrogen atoms and one more oxygen atoms (e.g., of a carbonyl group) and/or one or more nitrogen atoms (e.g., of an amine group and/or imine group). Without wishing to be bound by theory, interconnection of the fused aromatic system via hydrogen-bonding interactions may advantageously facilitate electronic charge delocalization and diffusion of ionic charges through the fused aromatic system. In some embodiments, interconnection of the fused aromatic system via hydrogen-bonding may also advantageously result in a solid material that is insoluble in organic and aqueous media, thereby providing a suitable material for use in electrodes.

The fused aromatic system may have any of a variety of suitable hydrogen-bonding interactions. In some embodiments, for example, the number of hydrogen-bonding interactions in the fused aromatic system is greater than or equal to 0.1, greater than or equal to 0.2, greater than or equal to 0.3, greater than or equal to 0.4, greater than or equal to 0.5, greater than or equal to 0.6, greater than or equal to 0.7, greater than or equal to 0.8, or greater than or equal to 0.9 hydrogen-bonds per mole of carbon atoms in the fused aromatic system. In certain embodiments, the number of hydrogen-bonding interactions in the fused aromatic system is less than or equal to 1, less than or equal to 0.9, less than or equal to 0.8, less than or equal to 0.7, less than or equal to 0.6, less than or equal to 0.5, less than or equal to 0.4, less than or equal to 0.3, or less than or equal to 0.2 hydrogen-bonds per mole of carbon atoms in the fused aromatic system is between greater than or equal to 0.33 and less than or equal to 1 hydrogen-bonds per mole of carbon atoms. Combinations of the above recited ranges are also possible (e.g., the number of hydrogen-bonding interactions in the fused aromatic system is between greater than or equal to 0.1 and less than or equal to 1 hydrogen-bonds per mole of carbon atoms in the fused aromatic system, the number of hydrogen-bonding interactions in the fused aromatic system is between greater than or equal to 0.3 and less than or equal to 0.3 hydrogen-bonds per mole of carbon atoms in the fused aromatic system). Other ranges are also possible. In certain embodiments, the number of hydrogen-bonding interactions in the fused aromatic system may be determined by structural and elemental analysis.

The fused aromatic system may have any of a variety of suitable π-π interactions (e.g., donor-accept π-π interactions). For example, in certain embodiments, at least a portion of the fused aromatic system is configured in a stacked and/or three-dimensional configuration via one or more π-π interactions. Without wishing to be bound by theory, interconnection of the fused aromatic system via π-π interactions may advantageously facilitate electronic charge delocalization and diffusion of ionic charges through the fused aromatic system. In some embodiments, interconnection of the fused aromatic system via π-π may also advantageously result in a solid material that is insoluble in organic and aqueous media, thereby providing a suitable material for use in electrodes.

In some embodiments, the average interlayer distance between the portion of the fused aromatic system configured in a stacked and/or three-dimensional configuration via one or more π-π interactions may be greater than or equal to 2 Å, greater than or equal to 2.5 Å, greater than or equal to 3 Å, or greater than or equal to 3.5 Å. In certain embodiments, the average interlayer distance between the portion of the fused aromatic system configured in a stacked and/or three-dimensional configuration via one or more π-π interactions may be less than or equal to 4 Å, less than or equal to 3.5 Å, less than or equal to 3 Å, or less than or equal to 2.5 Å. Combinations of the above recited ranges are also possible (e.g., the average interlayer distance between the portion of the fused aromatic system configured in a stacked and/or three-dimensional configuration via one or more π-π interactions is between greater than or equal to 2 Å and less than or equal to 4 Å, the average interlayer distance between the portion of the fused aromatic system configured in a stacked and/or three-dimensional configuration via one or more π-π interactions is between greater than or equal to 3 Å and less than or equal to 3.5 Å). Other ranges are also possible. In certain embodiments, the average interlayer distance between the portion of the fused aromatic system configured in a stacked and/or three-dimensional configuration via one or more π-π interactions may be determined by structural analysis and/or microscopic methods.

As explained herein, the composition may have low solubility in organic and aqueous solvents at ambient temperature and pressure due at least in part to the hydrogen-bonding interactions and/or π-π interactions of the fused aromatic system. In some embodiments, it may be advantageous for the composition to have a low solubility in organic and aqueous solvents, as the fused aromatic system may be used as an electrode active material.

The fused aromatic system may have any of a variety of suitable solubilities. In certain embodiments, for example, the fused aromatic system has a solubility less than or equal to less than or equal to 2 millimoles per liter of solvent (e.g., water and/or an organic solvent), less than or equal to 1.5 millimoles per liter of solvent, less than or equal to 1 millimole per liter of solvent, less than or equal to 0.5 millimoles per liter of solvent, or less. According to some embodiments, the fused aromatic system has a solubility greater than 0 millimoles per liter of solvent (e.g., water and/or organic solvent), greater than or equal to 0.1 millimoles per liter of solvent, greater than or equal to 0.5 millimoles per liter of solvent, greater than or equal to 1 millimole per liter of solvent, or greater than or equal to 1.5 millimoles per liter of solvent per liter of solvent. Combinations of the above recited ranges are also possible (e.g., the fused aromatic system has a solubility between less than or equal to 2 millimoles per liter of solvent and greater than 0 millimoles per liter of solvent, the fused aromatic system has a solubility between greater than or equal to 0.5 millimoles per liter of solvent and less than or equal to 1.5 millimoles per liter of solvent). Other ranges are also possible.

According to some embodiments, the composition comprises a molecule of the structure (and/or a plurality of molecules of the structure):

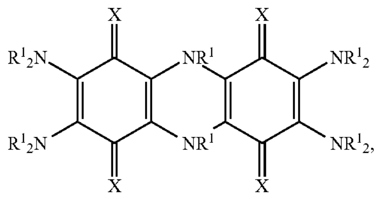

wherein X is selected from the group consisting of O, S, Se, or $NR^1$, and wherein each $R^1$ is the same or different and is selected from the group consisting of hydrogen (—H), optionally substituted alkyl (e.g., $—CH_3$), optionally substituted alkenyl (e.g., $—CH{=}CH_2$), or optionally substituted alkynyl (e.g., —C≡CH). Tautomers and/or isomers of the structure shown above are also possible, in some embodiments.

In certain embodiments, for example, the composition comprises tetraamino-dihydrophenazine-1,4,6,9-tetrone, referred to herein as bis-tetraamino-benzoquinone (BTABQ). In certain embodiments, BTABQ has the structure:

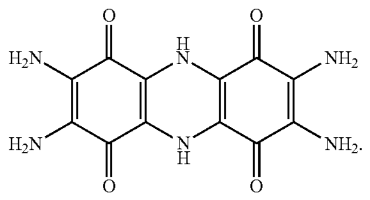 [SMILES: Nc1c(N)c(=O)c2[nH]c3c(=O)c(N)c(N)c(=O)c3[nH]c2c1=O]

In some embodiments, the composition comprises a plurality of BTABQ molecules. Tautomers and/or isomers of the BTABQ structure shown above are also possible, in some embodiments.

According to certain embodiments, BTABQ may be synthesized from a tetraamino-p-benzoquinone (TABQ) molecule of the structure:

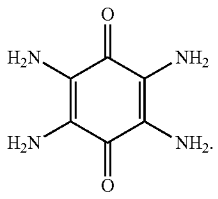 [SMILES: NC1=C(N)C(=O)C(N)=C(N)C1=O]

TABQ may be purchased commercially and/or synthesized using techniques known to a person of ordinary skill in the art. According to some embodiments, BTABQ may be formed from TABQ via a one-step Michael addition and elimination with a loss of ammonia.

According to certain embodiments, the composition comprises an oligomer and/or polymer of BTABQ (and/or a plurality of oligomers and/or polymers of BTABQ). The oligomer and/or polymer of BTABQ may take any of a variety of suitable forms. In some embodiments, for example, the oligomer and/or polymer of BTABQ is of the structure:

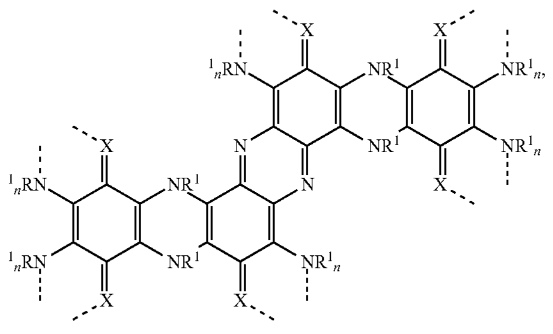

wherein each dotted line independently represents either a bond of another aromatic ring of the fused aromatic system or a terminal end of the fused aromatic system. In some embodiments wherein a dotted line represents a bond of another aromatic ring of the fused aromatic system, X may be N, $R^1$ may be selected from the group consisting of hydrogen (—H), optionally substituted alkyl (e.g., $—CH_3$), optionally substituted alkenyl (e.g., $CH{=}CH_2$), or optionally substituted alkynyl (e.g., —C≡CH), and n may be 1. In certain embodiments wherein a dotted line represents a terminal end of the fused aromatic system, X may be selected from the group consisting of O, S, Se, or $NR^1$, $R^1$ may be selected from the group consisting of hydrogen (—H), optionally substituted alkyl (e.g., $—CH_3$), optionally substituted alkenyl (e.g., $—CH{=}CH_2$), or optionally substituted alkynyl (e.g., —C≡CH), and n may be 2. Tautomers and/or isomers of the structure shown above are also possible, in some embodiments.

As would generally be understood by a person of ordinary skill in the art, in certain embodiments wherein a dotted line represents a bond of another aromatic ring of the fused aromatic system, the fused aromatic system may continue to extend, via one or more fused aromatic rings, beyond the aromatic ring formed by the bond represented by the dotted line.

In some embodiments, the oligomer and/or polymer of BTABQ is of the structure:

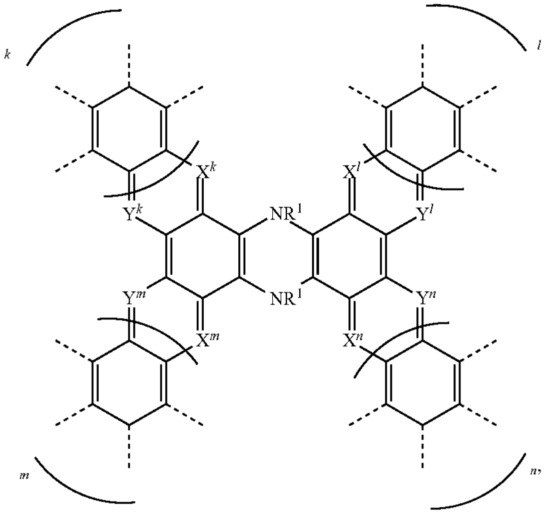

wherein when k is greater than 0, $X^k$ and $Y^k$ are N; when k is 0, $X^k$ is O and $Y^k$ is $NR^1$; when 1 is greater than 0, $X^1$ and $Y^1$ are N; when k is 0, $X^1$ is O and $Y^1$ is $NR^1$; when m is greater than 0, X" and Y" are N; when m is 0, X" is O and Y" is $NR^1$; when n is greater than 0, X" and Y" are N; when n is 0, X" is O and Y" is $NR^1$, and wherein $R^1$ is selected from the group consisting of hydrogen (—H), optionally substituted alkyl (e.g., $—CH_3$), optionally substituted alkenyl (e.g., $—CH{=}CH_2$), or optionally substituted alkynyl (e.g., —C≡CH)

In some non-limiting embodiments, the oligomer and/or polymer of BTABQ has the structure:

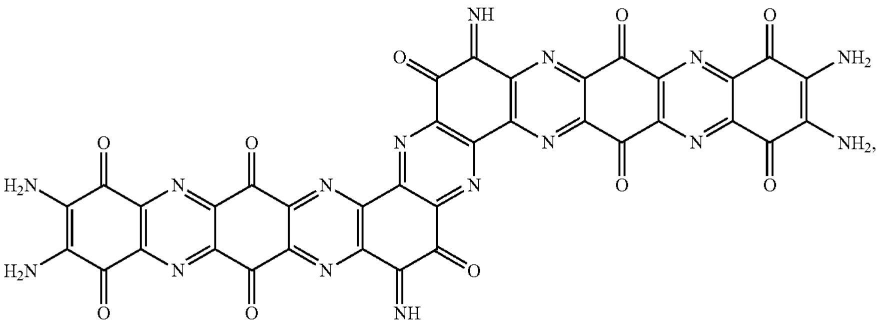

, or

-continued

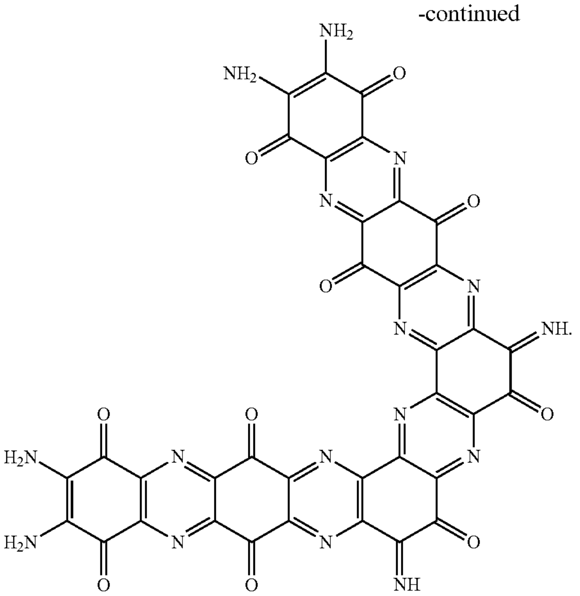

Tautomers and/or other isomers of the structures shown above are also possible.

The structure of the oligomer and/or polymer of BTABQ may be determined, in some embodiments, based on elemental analysis, matrix-assisted laser desorption/ionization-time of flight (MALDI-TOF) mass spectrometry, and/or X-ray photoelectron spectroscopy.

According to certain embodiments, the oligomer and/or polymer of BTABQ may be synthesized via polycondensation of BTABQ in the presence of heat with a loss of water. In some embodiments, the polycondensation reaction may be a ladderization reaction.

According to some embodiments, an electrode is described. The electrode is or comprises, in some embodiments, an electrochemically active charge storage material. As explained in further detail herein, the electrode may, in some embodiments, be disposed in an electrochemical cell (e.g., a battery) and/or a charge storage device (e.g., a capacitor).

FIG. 1 shows, according to certain embodiments, a schematic diagram of an electrode. In certain embodiments, electrode 102 is a composite electrode comprising at least two different (e.g., chemically distinct) materials. In some embodiments, for example, electrode 102 comprises active material 104. The active material is or comprises, in some embodiments, a composition as described herein. In certain embodiments, for example, the active material comprises an organic material (e.g., a fused aromatic system, such as BTABQ and/or a tautomer, oligomer, and/or polymer thereof). According to some embodiments, electrode 102 may comprise one or more additives.

The composite electrode (e.g., electrochemically active charge storage material) may comprise the active material in any of a variety of suitable amounts. In some embodiments, for example, the composite electrode comprises the active material in an amount greater than or equal to 50 weight percent (wt. %), greater than or equal to 60 wt. %, greater than or equal to 70 wt. %, greater than or equal to 80 wt. %, greater than or equal to 90 wt. %, or greater than or equal to 95 wt. % versus the total weight of the composite electrode. In certain embodiments, the composite electrode comprises the active material in an amount less than or equal to 99 wt. %, less than or equal to 95 wt. %, less than or equal to 90 wt. %, less than or equal to 80 wt. %, less than or equal to 70 wt. %, or less than or equal to 60 wt. % versus the total weight of the composite electrode. Combinations of the above recited ranges are possible (e.g., the composite electrode comprises the active material in an amount between greater than or equal to 50 wt. % and less than or equal to 99 wt. % versus the total weight of the composite electrode, the composite electrode comprises the active material in an amount between greater than or equal to 80 wt. % and less than or equal to 90 wt. % versus the total weight of the composite electrode). Other ranges are also possible.

As mentioned above, the composite electrode (e.g., electrochemically active charge storage material) may comprise one or more additives. Suitable additives include, but are not limited to, a conductive species and/or a binder. Suitable conductive species include, for example, conductive carbon materials (e.g., acetylene black carbon). In certain embodiments, suitable binders include polymers (e.g., polyvinylidene fluoride).

The composite electrode (e.g., electrochemically active charge storage material) may comprise the one or more additives in any of a variety of suitable amounts. In some embodiments, for example, the composite electrode comprises the one or more additives in an amount greater than or equal to 1 wt. %, greater than or equal to 10 wt. %, greater than or equal to 20 wt. %, greater than or equal to 30 wt. %, or greater than or equal to 40 wt. % versus the total weight of the composite electrode. In certain embodiments, the composite electrode comprises one or more additives in an amount less than or equal to 50 wt. %, less than or equal to 40 wt. %, less than or equal to 30 wt. %, less than or equal to 20 wt. %, or less than or equal to 10 wt. % versus the total weight of the composite electrode. Combinations of the above recited ranges are possible (e.g., the composite electrode comprises the one or more additives in an amount between greater than or equal to 1 wt. % and less than or equal to 50 wt. % versus the total weight of the composite electrode, the composite electrode comprises the one or more additives in an amount between greater than or equal to 10 wt. % and less than or equal to 30 wt. % versus the total weight of the composite electrode). Other ranges are also possible.

An electrode as described herein may be fabricated using techniques known to a person of ordinary skill in the art. In certain embodiments, for example, appropriate ratios of electrode materials may be mixed together, coated onto a substrate, and dried. In certain non-limiting embodiments, for example, active material, conductive material, and binder may be mixed together in an 8:1:1 ratio in an organic solvent, coated onto a carbon substrate, and dried.

According to certain embodiments, an electrochemical cell is described. As would generally be understood by a person of ordinary skill in the art, the electrochemical cell may comprise one or more electrodes (e.g., one or more electrochemically active charge storage materials). In certain embodiments, the electrochemical cell is a battery (e.g., a rechargeable or non-rechargeable battery).

Figure 2:
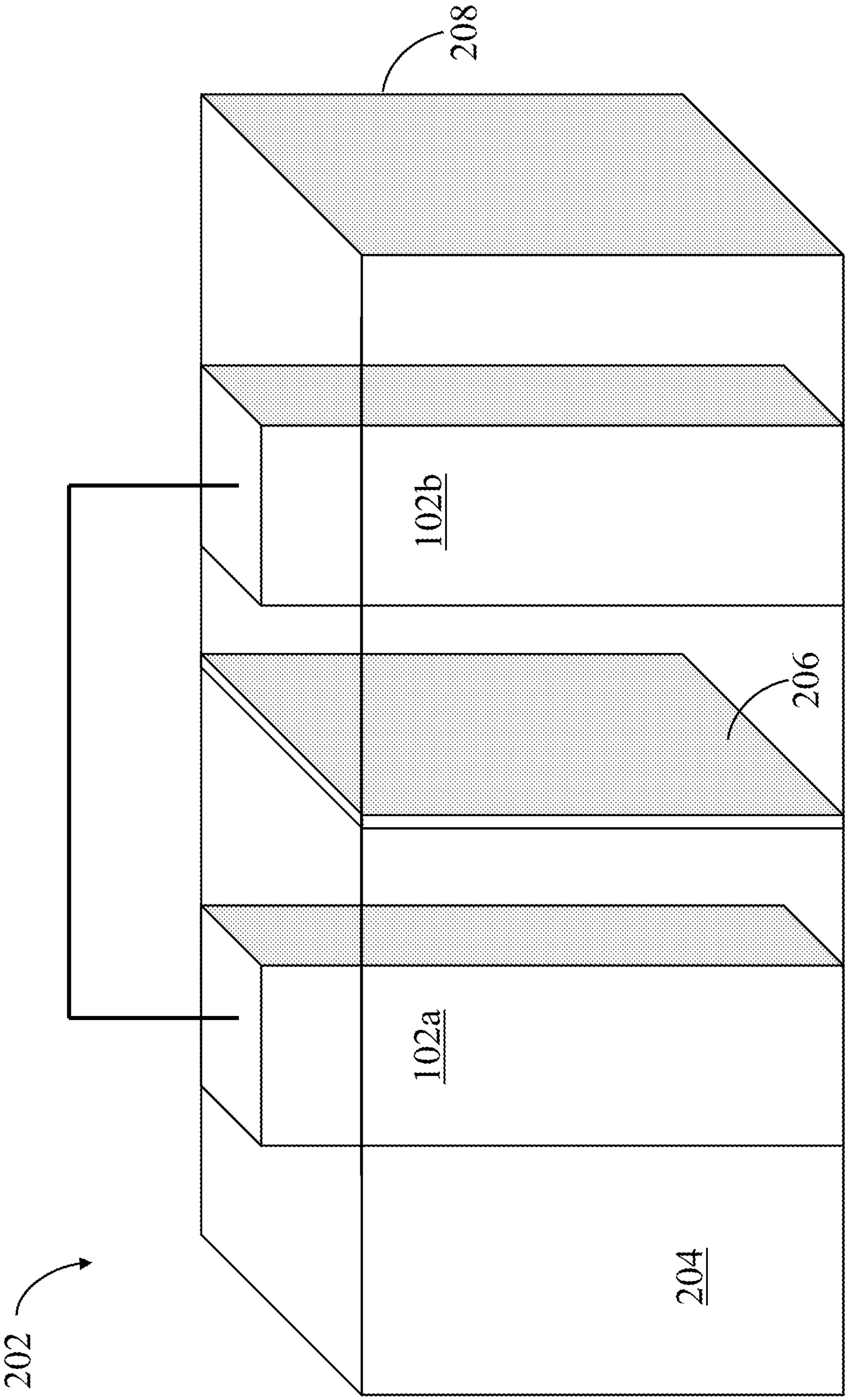
FIG. 2 shows, according to certain embodiments, a schematic diagram of an electrochemical cell.

FIG. 2 shows, according to certain embodiments, a schematic diagram of an electrochemical cell. In some embodiments, electrochemical cell 202 comprises first electrode 102*a* and second electrode 102*b*. First electrode 102*a* and second electrode 102*b* may, in some embodiments, be disposed in housing 208. In certain embodiments, at least one of first electrode 102*a* and/or second electrode 102*b* comprises an active material comprising a composition as described herein. In some embodiments, for example, the active material of at least one electrode comprises an organic material (e.g., a fused aromatic system, such as BTABQ and/or a tautomer, oligomer, and/or polymer thereof).

According to some embodiments, electrochemical cell 202 comprises electrolyte 204. Electrolyte 204 may, in some embodiments, be disposed in housing 208. In certain embodiments, electrolyte 204 is a liquid electrolyte. In other embodiments, electrolyte 204 is a solid electrolyte. Further details regarding the liquid electrolyte and solid electrolyte are described herein.

The liquid electrolyte may have any of a variety of suitable pH values. In some embodiments, for example, the liquid electrolyte is sufficiently acidic and has a pH greater than or equal to 0, greater than or equal to 0.5, greater than or equal to 1, or greater than or equal to 1.5. In certain embodiments, the liquid electrolyte is sufficiently acidic and has a pH less than or equal to 2, less than or equal to 1.5, less than or equal to 1, or less than or equal to 0.5. Combinations of the above recited ranges are possible (e.g., the liquid electrolyte is sufficiently acidic and has a pH between greater than or equal to 0 and less than or equal to 2, the liquid electrolyte is sufficiently acidic and has a pH between greater than or equal to 1 and less than or equal to 1.5). Other ranges are also possible.

According to some embodiments, the liquid electrolyte may be sufficiently basic and may have a pH greater than or equal to 12, greater than or equal to 12.5, greater than or equal to 13, greater than or equal to 13.5, greater than or equal to 14, or greater than or equal to 14.5. In certain embodiments, the liquid electrolyte is sufficiently basic and has a pH less than or equal to 15, less than or equal to 14.5, less than or equal to 14, less than or equal to 13.5, less than or equal to 13, or less than or equal to 12.5. Combinations of the above recited ranges are possible (e.g., the liquid electrolyte is sufficiently basic and has a pH between greater than or equal to 12 and less than or equal to 15, the liquid electrolyte is sufficiently basic and has a pH between greater than or equal to 13 and less than or equal to 13.5). Other ranges are also possible.

The pH of the liquid electrolyte may be determined, in some embodiments, using a PH meter.

As will be explained in further detail below, a liquid electrolyte with a sufficiently acidic pH (e.g., greater than or equal to 0 and less than 2) and/or a sufficiently basic pH (e.g., greater than 12 and less than or equal 14) may advantageously enhance the charge capacity of an electrode disposed in the liquid electrolyte as compared to more neutral pH values (e.g., greater than or equal to 4 and less than or equal 10).

In some embodiments, electrochemical cell 202 comprises separator 206 disposed between first electrode 102*a* and second electrode 102*b*. Separator 206 may, in some embodiments, be disposed in housing 208. Further details regarding the separator are described herein.

According to certain embodiments, a charge storage device is described. As would generally be understood by a person of ordinary skill in the art, the charge storage device comprises, in some embodiments, one or more electrodes (e.g., one or more electrochemically active charge storage materials). The charge storage device may, in some embodiments, be a capacitor or a supercapacitor.

Figure 3:
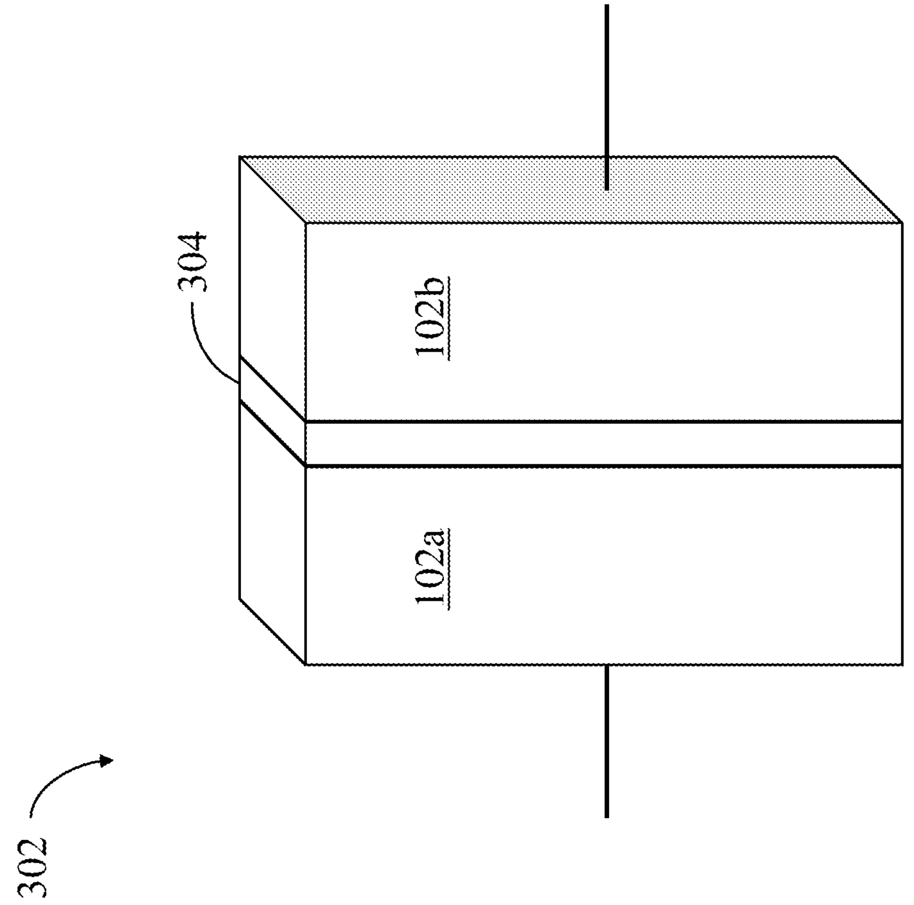
FIG. 3 shows, according to certain embodiments, a schematic diagram of a charge storage device.

FIG. 3 shows, according to certain embodiments, a schematic diagram of a charge storage device. In some embodiments, charge storage device 302 comprises first electrode 102*a* and second electrode 102*b*. At least one of first electrode 102*a* and/or second electrode 102*b* comprises, in certain embodiments, an active material comprising a composition as described herein. In some embodiments, for example, the active material comprises an organic material (e.g., a fused aromatic system, such as BTABQ and/or a tautomer, oligomer, and/or polymer thereof).

In some embodiments, charge storage device 302 comprises insulator 304 disposed between first electrode 102*a* and second electrode 102*b*. According to certain embodiments, insulator 304 may be a dielectric material.

The electrode (e.g., electrochemically active charge storage material) may have any of a variety of suitable electrical conductivities. In some embodiments, for example, the electrode has an electrical conductivity greater than or equal to $10^{-8}$ S/cm, greater than or equal to $10^{-7}$ S/cm, greater than or equal to $10^{-6}$ S/cm, greater than or equal to $10^{-5}$ S/cm, greater than or equal to $10^{-4}$ S/cm, or greater than or equal to $10^{-3}$ S/cm. In certain embodiments, the electrode has an electrical conductivity less than or equal to $10^{-2}$ S/cm, less than or equal to $10^{-3}$ S/cm, less than or equal to $10^{-4}$ S/cm, less than or equal to $10^{-5}$ S/cm, less than or equal to $10^{-6}$ S/cm, or less than or equal to $10^{-7}$ S/cm. Combinations of the above recited ranges are possible (e.g., the electrode has an electrical conductivity between greater than or equal to $10^{-8}$ S/cm and less than or equal to $10^{-2}$ S/cm, the electrode has an electrical conductivity between greater than or equal to $10^{-6}$ S/cm and less than or equal to $10^{-4}$ S/cm). Other ranges are also possible. The electrical conductivity of the electrode may be determined, in some embodiments, using a conductivity meter.

The electrode (e.g., electrochemically active charge storage material) may have any of a variety of suitable specific capacitances. In some embodiments, for example, the electrode has a specific capacitance greater than or equal to 200 F, greater than or equal to 250 F, greater than or equal to 300 F, greater than or equal to 350 F, greater than or equal to 400 F, greater than or equal to 450 F, greater than or equal to 500 F, greater than or equal to 550 F, greater than or equal to 600 F, or greater than or equal to 650 F per gram of active material. In certain embodiments, the electrode has a specific capacitance less than or equal to 700 F, less than or equal to 650 F, less than or equal to 600 F, less than or equal to 550 F. less than or equal to 500 F, less than or equal to 450 F, less than or equal to 400 F, less than or equal to 350 F, less than or equal to 300 F, or less than or equal to 250 F per gram of active material. Combinations of the above recited ranges are possible (e.g., the electrode has a specific capacitance between greater than or equal to 200 F and less than or equal to 700 F per gram of active material, the electrode has a specific capacitance between greater than or equal to 500 F and less than or equal to 550 F per gram of active material). Other ranges are also possible. The specific capacitance may be calculated, in some embodiments, from cyclic voltammetry (CV) data according to the following equation: $C=Q/(Vm)$, wherein C (F/g) is the specific capacitance, m (g) is the mass of the active material, Q (C) is the average charge during the charging and discharging process, and V (V) is the potential window. According to some embodiments, the specific capacitance is measured at a scan rate of 0.2 mV/s.

The electrode (e.g., electrochemically active charge storage material) may have any of a variety of suitable cycling performances. In some embodiments, for example, the electrode has a cycling performance greater than or equal to 10,000 cycles, greater than or equal to 20,000 cycles, greater than or equal to 30,000 cycles, greater than or equal to 40,000 cycles, greater than or equal to 50,000 cycles, greater than or equal to 60,000 cycles, greater than or equal to 70,000 cycles, greater than or equal to 80,000 cycles, or greater than or equal to 90,000 cycles. In certain embodiments, the electrode has a cycling performance less than or equal to 100,000 cycles, less than or equal to 90,000 cycles, less than or equal to 80,000 cycles, less than or equal to 70,000 cycles, less than or equal to 60,000 cycles, less than or equal to 50,000 cycles, less than or equal to 40,000 cycles, less than or equal to 30,000 cycles, or less than or equal to 20,000 cycles. Combinations of the above recited ranges are possible (e.g., the electrode has a cycling performance between greater than or equal to 10,000 cycles and less than or equal to 100,000 cycles, the electrode has a cycling performance between greater than or equal to 30,000 cycles and less than or equal to 40,000 cycles). Other ranges are also possible. According to certain embodiments, the cycling performance may be measured at a scan rate of 30 mV/s.

As explained above, the fused aromatic system may comprise a plurality of carbon atoms, hydrogen atoms, and one or more heteroatoms (e.g., N, O, S, and/or Se) replacing a carbon atom. The heteroatoms may advantageously act as redox-active sites that facilitate electric and/or ionic transport through the bulk of the material. In certain embodiments, a ratio of moles of electrons stored as charge per mole of heteroatoms in the fused aromatic system is greater than or equal to 0.1, greater than or equal to 0.2, greater than or equal to 0.3, greater than or equal to 0.4, greater than or equal to 0.5, greater than or equal to 0.6, or greater than or equal to 0.7. In some embodiments, a ratio of moles of electrons stored as charge per mole of heteroatoms in the fused aromatic system is less than or equal to 0.8, less than or equal to 0.7, less than or equal to 0.6, less than or equal to 0.5, less than or equal to 0.4, less than or equal to 0.3, or less than or equal to 0.2. Combinations of the above recited ranges are also possible (e.g., a ratio of moles of electrons stored as charge per mole of heteroatoms in the fused aromatic system is between greater than or equal to 0.1 and less than or equal to 0.8, a ratio of moles of electrons stored as charge per mole of heteroatoms in the fused aromatic system is between greater than or equal to 0.3 and less than or equal to 0.6). Other ranges are also possible.

The composite electrode (e.g., electrochemically active charge storage material) may have any of a variety of suitable charge capacities per gram of active material. In certain embodiments, for example, the composite electrode has a charge capacity greater than or equal to 50 mAh, greater than or equal to 100 mAh, greater than or equal to 150 mAh, greater than or equal to 200 mAh, greater than or equal to 250 mAh, greater than or equal to 300 mAh, or greater than or equal to 350 mAh per gram of active material. In some embodiments, the composite electrode has a charge capacity less than or equal to 400 mAh, less than or equal to 350 mAh, less than or equal to 300 mAh, less than or equal to 250 mAh, less than or equal to 200 mAh, less than or equal to 150 mAh, or less than or equal to 50 mAh. Combinations of the above recited ranges are possible (e.g., the composite electrode has a charge capacity between greater than or equal to 50 mAh and less than or equal to 400 mAh per gram of active material, the composite electrode has a charge capacity between greater than or equal to 150 mAh and less than or equal to 200 mAh per gram of active material). Other combinations are also possible.

The composite electrode (e.g., electrochemically active charge storage material) may have any of a variety of suitable charge capacities per gram of composite electrode. In some embodiments, for example, the composite electrode has a charge capacity greater than or equal to 30 mAh, greater than or equal to 50 mAh, greater than or equal to 100 mAh, greater than or equal to 150 mAh, greater than or equal to 200 mAh, greater than or equal to 250 mAh, or greater than or equal to 300 mAh per gram of composite electrode. In some embodiments, the composite electrode has a charge capacity less than or equal to 350 mAh, less than or equal to 300 mAh, less than or equal to 250 mAh, less than or equal to 200 mAh, less than or equal to 150 mAh, less than or equal to 100 mAh, or less than or equal to 50 mAh per gram of composite electrode. Combinations of the above recited ranges are possible (e.g., the composite electrode has a charge capacity between greater than or equal to 30 mAh and less than or equal to 350 mAh per gram of composite electrode, the composite electrode has a charge capacity between greater than or equal to 100 mAh and less than or equal to 150 mAh per gram of composite electrode). Other combinations are also possible.

According to certain embodiments, the charge capacities described above (i.e., the charge capacity per gram of active material and/or the charge capacity per gram of composite electrode) may be delivered at a relatively fast charge and/or discharge rate as compared to conventional capacitor systems. In some embodiments, for example, the charge capacity is delivered at charge and/or discharge rate that is less than 60 seconds, less than 50 seconds, less than 40 seconds, less than 30 seconds, or less than 20 seconds. In certain embodiments, the charge capacity is delivered at a charge and/or discharge rate that is greater than or equal to 10 seconds, greater than or equal to 20 seconds, greater than or equal to 30 second, greater than or equal to 40 seconds, or greater than or equal to 50 seconds. Combinations of the above recited ranges are also possible (e.g., the charge capacity is delivered at a charge and/or discharge rate that is between less than or equal to 60 seconds and greater than or equal to 10 seconds, the charge capacity is delivered at a charge and/or discharge rate that is greater than or equal to 30 seconds and less than or equal to 40 seconds). Other ranges are also possible.

As explained above, an electrode (e.g., an electrochemically active charge storage material) as described herein may be disposed in an electrochemical cell comprising an electrolyte (e.g., a liquid electrolyte). In some embodiments, the liquid electrolyte may have a sufficiently acidic pH (e.g., greater than or equal to 0 and less than 2)) or a sufficiently basic pH (e.g., greater than 12 and less than or equal 14). In some such embodiments, the electrode may have a charge capacity that is greater than the charge capacity of an electrode that is disposed in an electrochemical cell comprising a liquid electrolyte having a pH greater than or equal to 2 and less than or equal to 12 but is otherwise equivalent. Without wishing to be bound by theory, the increased charge capacities at sufficiently acidic and/or sufficiently basic liquid electrolyte pH values may originate from rapid pseudocapacitive intercalation processes of cations and/or anions throughout the electrode bulk.

In some embodiments, for example, the electrode has a charge capacity that is at least 20% greater, at least 30% greater, at least 40% greater, at least 50% greater, at least 60% greater, at least 70% greater, at least 80% greater, or at least 90% greater when the pH value of the liquid electrolyte is between greater than or equal to 0 and less than or equal to 2 or between greater than or equal to 12 and less than or equal to 15 as compared to when the pH value of the liquid electrolyte is between greater than 2 and less than 12. In certain embodiments, the electrode has a charge capacity that is less than 100% greater, less than or equal to 90% greater, less than or equal to 80% greater, less than or equal to 70% greater, less than or equal to 60% greater, less than or equal to 50% greater, less than or equal to 40% greater, or less than or equal to 30% greater when the pH value of the liquid electrolyte is between greater than or equal to 0 and less than or equal to 2 or between greater than or equal to 12 and less than or equal to 15 as compared to when the pH value of the liquid electrolyte is between greater than 2 and less than 12. Combinations of the above recited ranges are also possible (e.g., the electrode has a charge capacity that is between at least 20% greater and less than 100% greater when the pH value of the liquid electrolyte is between greater than or equal to 0 and less than or equal to 2 or between greater than or equal to 12 and less than or equal to 15 as compared to when the pH value of the liquid electrolyte is between greater than 2 and less than o 12, the electrode has a charge capacity that is between at least 40% greater and less than or equal to 60% greater when the pH value of the liquid electrolyte is between greater than or equal to 0 and less than or equal to 2 or between greater than or equal to 12 and less than or equal to 15 as compared to when the pH value of the liquid electrolyte is between greater than 2 and less than 12). Other ranges are also possible.

In some embodiments, the electrode (e.g., electrochemically active charge storage material) may advantageously retain a high amount of charge capacity after cycling the electrode. In some embodiments, for example, the electrode has greater than or equal to 75% charge capacity retention, greater than or equal to 80% charge capacity retention, greater than or equal to 85% charge capacity retention, greater than or equal to 90% charge capacity retention, or greater than or equal to 95% charge capacity retention after at least 20,000 cycles. In certain embodiments, the electrode has less than or equal to 99% charge capacity retention, less than or equal to 95% charge capacity retention, less than or equal to 90% charge capacity retention, less than or equal to 85% charge capacity retention, or less than or equal to 80% charge capacity retention after at least 20,000 cycles. Combinations of the above recited ranges are also possible (e.g., the electrode has between greater than or equal to 75% and less than 99% charge capacity retention after at least 20,000 cycles, the electrode has between greater than or equal to 85% and less than or equal to 95% charge capacity retention after at least 20,000 cycles). Other ranges are also possible.

According to certain embodiments, the electrode (e.g., electrochemically active charge storage material) may advantageously deliver a sufficiently high amount of its charge capacity. In some embodiments, for example, the electrode delivers at least 80%, at least 85%, at least 90%, at least 95%, or at least 99% of its charge capacity at a voltage higher than 2.0 V vs. $Li^+/Li$ standard reference electrode. In certain embodiments, the electrode delivers less than 100%, less than or equal to 99%, less than or equal to 95%, less than or equal to 90% or less than or equal to 85% of its charge capacity at a voltage higher than 2.0 V vs. $Li^+/Li$ standard reference electrode. Combinations of the above recited ranges are also possible (e.g., the electrode delivers between at least 80% and less than 100% of its charge capacity at a voltage higher than 2.0 V vs. Lit/Li standard reference electrode, the electrode delivers between at least 85% and less than 95% of its charge capacity at a voltage higher than 2.0 V vs. $Li^+/Li$ standard reference electrode). Other ranges are also possible.

As noted above, in certain embodiments, an electrochemical cell and/or charge storage device as described herein may comprise one or more electrodes. For example, in certain embodiments, the electrochemical cell and/or charge storage device comprises an anode and a cathode.

The anode may comprise a variety of anode active materials. As used herein, the term "anode active material" refers to any electrochemically active species associated with the anode.

In some embodiments, the anode may have a thickness of less than or equal to 1500 micrometers, less than or equal to 1250 micrometers, less than or equal to 1000 micrometers, less than or equal to 750 micrometers, less than or equal to 500 micrometers, or less than or equal to 200 micrometers. In certain embodiments, the anode may have a thickness of at least 1 micrometer, at least 5 micrometers, at least 10 micrometers, at least 25 micrometers, at least 50 micrometers, at least 100 micrometers, or at least 150 micrometers. Combinations of the above-referenced ranges are also possible (e.g., from 1 micrometer to 1500 micrometers). Other ranges are also possible.

The cathode may comprise a variety of cathode active materials. As used herein, the term "cathode active material" refers to any electrochemically active species associated with the cathode.

In some embodiments, the cathode may have a thickness of less than or equal to 2000 micrometers, less than or equal to 1500 micrometers, less than or equal to 1250 micrometers, less than or equal to 1000 micrometers, less than or equal to 750 micrometers, less than or equal to 500 micrometers, or less than or equal to 200 micrometers. In certain embodiments, the cathode may have a thickness of at least 1 micrometer, at least 5 micrometers, at least 10 micrometers, at least 25 micrometers, at least 50 micrometers, at least 100 micrometers, or at least 150 micrometers. Combinations of the above-referenced ranges are also possible (e.g., from 1 micrometer to 2000 micrometers). Other ranges are also possible.

As described herein, the electrochemical cell may, in some embodiments, comprise an electrolyte. As would generally be understood by a person of ordinary skill in the art, electrolytes used in electrochemical cells can function as a medium for the storage and transport of ions, and in the special case of solid and/or gel electrolytes, these materials may additionally function as a separator between the anode and the cathode. Any liquid, solid, or gel material capable of storing and transporting ions may be used, so long as the material facilitates the transport of ions between the anode and the cathode. The electrolyte is generally electronically non-conductive to prevent short circuiting between the anode and the cathode. The electrolyte can comprise one or more liquid electrolyte solvents, gel polymer materials, or polymer materials. The electrolyte may also comprise one or more ionic electrolyte salts to provide and/or enhance ionic conductivity.

In some cases, the electrochemical chemical cell comprises a liquid electrolyte. In certain embodiments, the liquid electrolyte is an aqueous electrolyte (e.g., water). The aqueous electrolyte may, in some embodiments, contain other components, such one or more ionic electrolyte salts (e.g., to provide and/or enhance ionic conductivity).

In certain embodiments, the electrolyte includes a non-aqueous electrolyte.

Suitable non-aqueous electrolytes include organic liquid electrolyte solvents. These electrolytes may optionally include one or more ionic electrolyte salts (e.g., to provide and/or enhance ionic conductivity). Examples of useful non-aqueous organic liquid electrolyte solvents include, but are not limited to, acetonitrile. Other non-aqueous organic liquid electrolyte solvents are possible, as the disclosure is not meant to be limiting in this regard.

According to certain embodiments, the electrochemical cell comprises a solid and/or gel electrolyte. For example, in some embodiments, one or more solid polymers can be used to form a solid and/or gel electrolyte.

The electrolyte may further comprise one or more ionic electrolyte salts, generally known in the art, to provide and/or enhance the ionic conductivity of the electrolyte. For example, in some cases, the ionic electrolyte salt may be a chloride salt (e.g., NaCl), a hydrogen phosphate salt ($Na_2HPO_4$), a carbonate salt ($Na_2CO_3$), and/or citric acid. Other ionic electrolyte salts are also possible, as the disclosure is not meant to be limiting in this regard.

In some embodiments, an electrochemical cell includes a separator. The separator generally comprises a polymeric material. In some embodiments, the separator is located between the electrolyte and an electrode (e.g., a first electrode, a second electrode, an anode, a cathode). The separator can be configured to inhibit (e.g., prevent) physical contact between a first electrode and a second electrode, which could result in short circuiting of the electrochemical cell. The separator can be configured to be substantially electronically non-conductive, which can inhibit the degree to which the separator causes short circuiting of the electrochemical cell.

The following examples are intended to illustrate certain embodiments of the present invention, but do not exemplify the full scope of the invention.

Example 1

The following example describes the synthesis and characterization of bis-tetraamino-benzoquinone (BTABQ) molecules and polymers thereof (pBTABQ).

Figure 5:
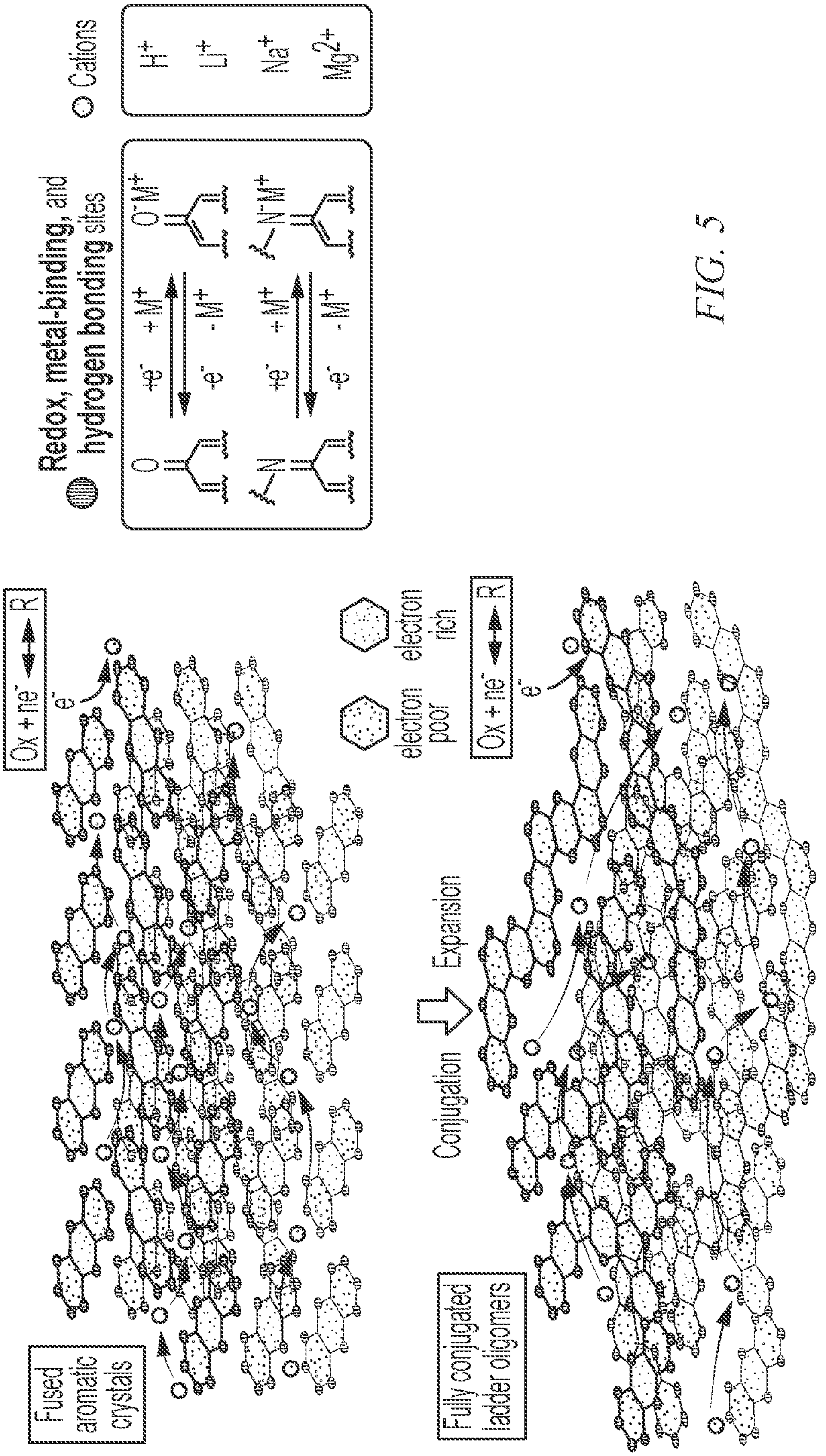
FIG. 5 shows, according to certain embodiments, a schematic representation of fused aromatic molecular crystals and their conversion to conjugated ladder oligomers through self-condensation.
Figure 6:
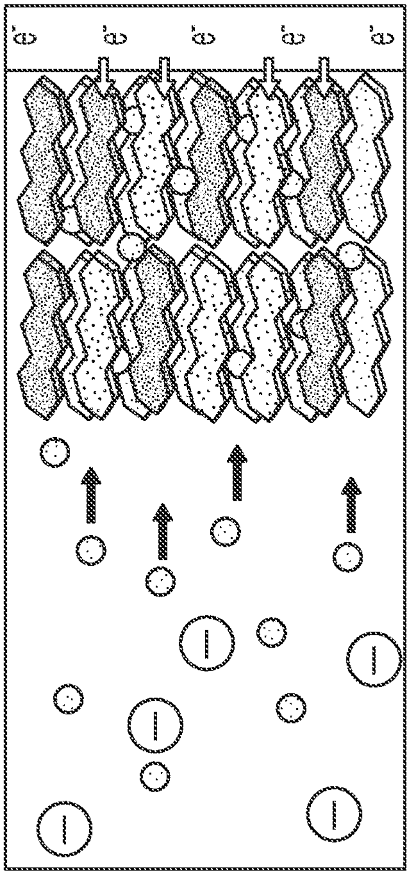
FIG. 6 shows, according to certain embodiments, a schematic representation of pseudocapacitive intercalation of various cations into fused aromatic materials.

Fused aromatic materials comprising BTABQ and pBTABQ may be used as electrodes for electrochemical energy storage (EES). The materials possess dense redox-active quinone/imine groups (e.g., C:(N/O)<1.3) in aromatic molecular backbones with extended conjugation (FIG. 4), which form insoluble solids, in both organic and aqueous media, through strong intermolecular hydrogen bonding and donor-acceptor (D-A) T-IL interactions (FIG. 5). BTABQ and pBTABQ exhibit excellent charge-storage capacities at high charge-discharge rates in various electrolytes, primarily originating from rapid pseudocapacitive intercalation processes (FIG. 6) throughout the electrode bulk, even at practical mass loadings, due to excellent electronic delocalization and facile ion transport.

Figure 4:
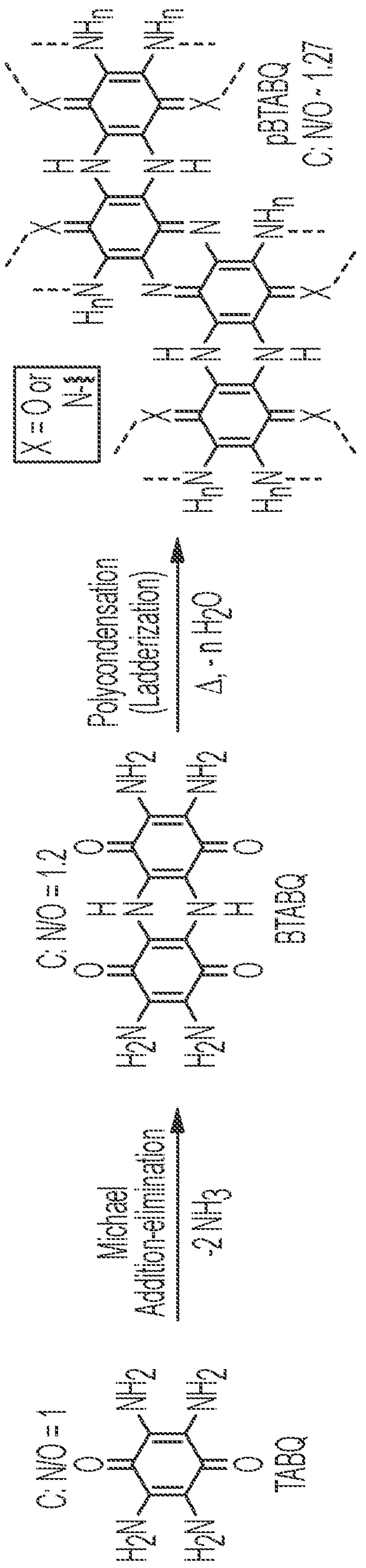
FIG. 4 shows, according to certain embodiments, the synthesis of a bis-tetraamino-benzoquinone (BTABQ) and a polymer thereof (pBTABQ)
Figure 7:
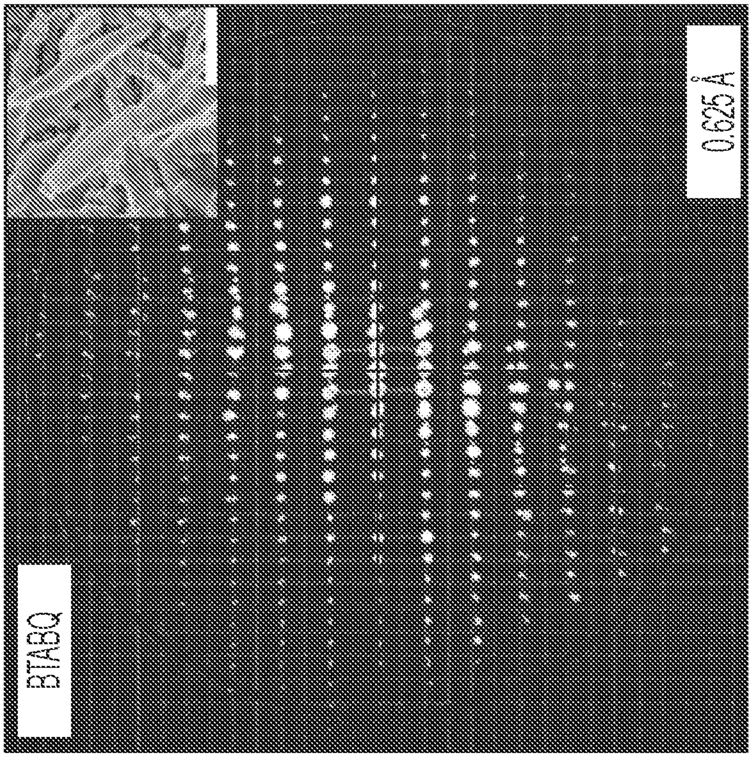
FIG. 7 shows, according to certain embodiments, three-dimensional (3D) reciprocal lattices of BTABQ with a maximum resolution of 0.625 Å, wherein the inset shows a scanning electron microscopy (SEM) image of BTABQ rods (scale bar: 2 μm)
Figure 8:
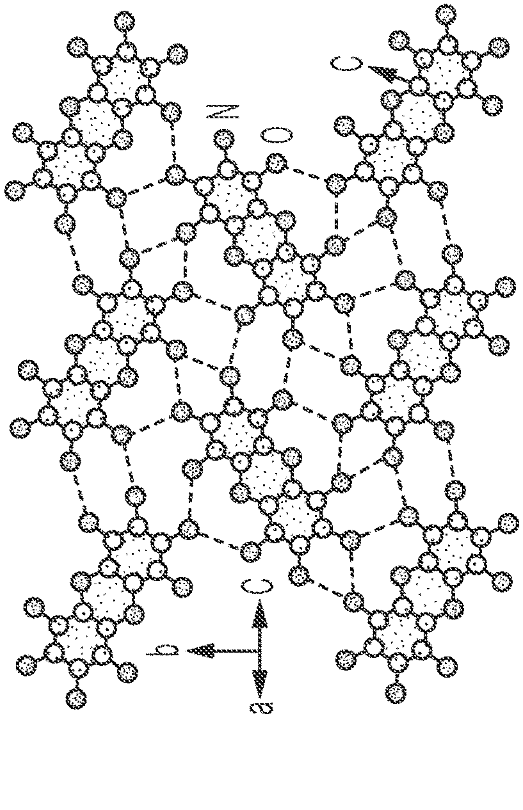
FIG. 8 shows, according to certain embodiments, a schematic representation of a two-dimensional (2D) layer of BTABQ molecules formed by hydrogen bonding interactions.
Figure 9:
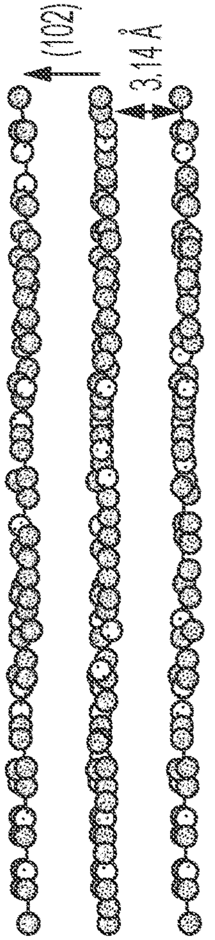
FIG. 9 shows, according to certain embodiments, a schematic representation of $\pi$-$\pi$ stacking of 2D layers of BTABQ.
Figure 10:
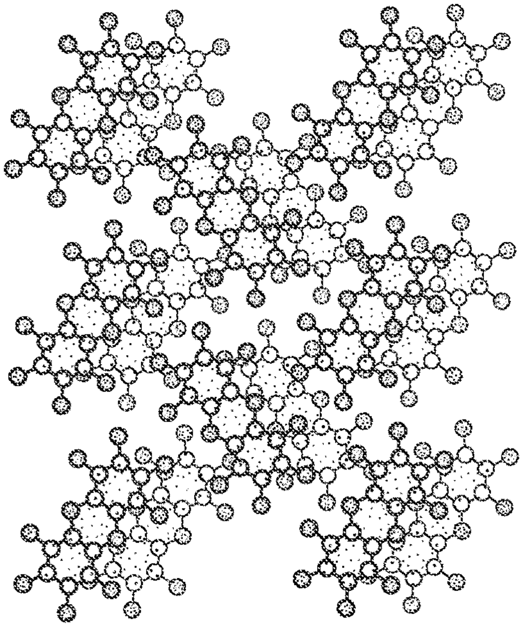
FIG. 10 shows, according to certain embodiments, a schematic representation of donor-acceptor alignment of 2D layers of BTABQ.

One-step Michael addition and elimination of tetraaminobenzoquinone (TABQ) produces BTABQ in gram scale (FIG. 4). While highly insoluble in common organic solvents, BTABQ appears as crystalline micro-rods (FIG. 7), as revealed by powder X-ray diffraction (PXRD). The crystal structure of BTABQ was obtained through Pawley refinement of the synchrotron PXRD data and continuous rotation electron diffraction (cRED) with the ab initio method. The high resolution of cRED datasets, down to 0.625 Å, allows direct location of all non-hydrogen atoms. BTABQ has a planar fused aromatic backbone, and each BTABQ molecule is closely surrounded by six neighbors, forming two-dimensional (2D) layers through strong intermolecular hydrogen bonds (FIG. 8). 2D layers stack through donor-acceptor (D-A) π-π interaction with a short interlayer separation, 3.14 Å (FIG. 9, FIG. 10). Experimental indexing of a BTABQ single crystal reveals that the long axis of the crystal corresponds to the (102) crystallographic direction (i.e., normal to the 2D layers), whereas its cross section is parallel to the 2D layers. Exfoliated BTABQ crystals further evidence the 2D layered nature. Altogether, the anisotropic crystal growth and 2D nature of BTABQ indicate that intermolecular hydrogen bonds are stronger than interlayer π-π stacking. Overall, the dense and energetically favorable solid-state packing of BTABQ offers potential for efficient electronic delocalization.

Considering the close proximity of amino and carbonyl groups in the 2D layers, it was envisioned that BTABQ may undergo solid-state poly-condensation to produce a more extended material. The thermogravimetric profile of BTABQ reveals a notable weight loss at around 300° C., supporting the possibility for such a ring-fusion. Indeed, heating BTABQ at ~300° C. under vacuum for 2 days lead to complete consumption of BTABQ and formation of an amorphous solid (pBTABQ) with unchanged particle sizes and morphology. pBTABQ has a significantly higher molecular weight and lower oxygen content than BTABQ, as expected for water loss during ladderization. Pair distribution function analyses of both materials reveal their similar local structures and indicate that, despite a lack of long-range ordering, pBTABQ has a dense solid-state arrangement of molecular fragments analogous to BTABQ. High magnification Cryo-EM images of pBTABQ confirmed its disordered but dense solid-state packing. Remarkably, pBTABQ still exhibits strong hydrogen bonding interactions similar to BTABQ. Gas sorption studies indicate that both materials are non-porous, given their low specific surface areas of ~20 $m^2/g$. Altogether, various characterizations confirm that pBTABQ is a disordered oligomeric analogue of BTBAQ that has expanded aromatic backbone, rich carbonyl/imine redox sites, strong hydrogen bonds, and dense solid-state packing.

Figure 11:
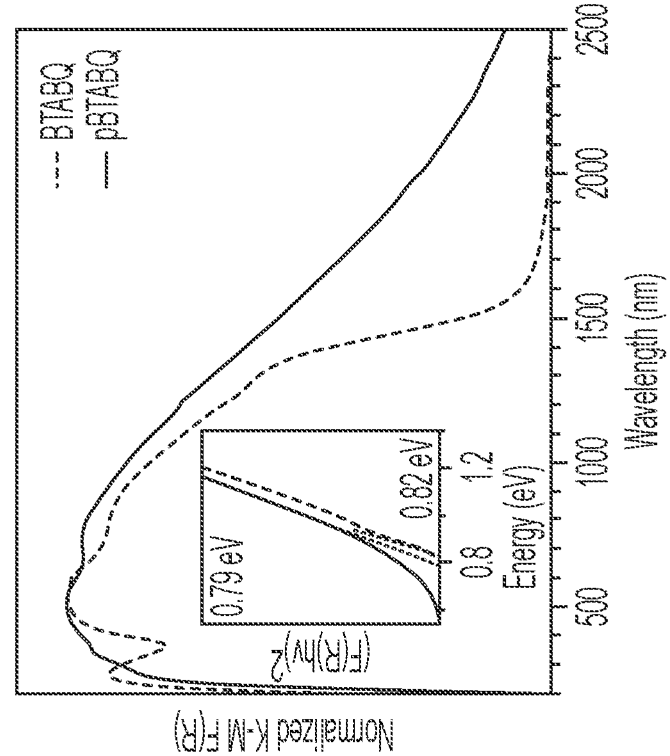
FIG. 11 shows, according to certain embodiments, diffuse reflectance ultraviolet-visible-near infrared (DRUV-Vis-NIR) spectra of BTABQ and pBTABQ.

The electronic properties of BTABQ and pBTABQ were characterized by diffuse-reflectance UV-Vis (DRUV-Vis) spectroscopy. Both materials exhibit broad absorption centered around 520 and 800 nm (FIG. 11). While the former originates from intra-quinone transition, extended conjugation within fused aromatic backbones of BTABQ and pBTABQ accounts for the latter. Remarkably, both materials display significant absorptions in the near-infrared region (NIR), leading to narrow optical band gaps of 0.82 eV and 0.79 eV (FIG. 11, inset) for BTABQ and pBTABQ, respectively. The intense NIR adsorptions are mainly due to bulk electronic delocalization through extended conjugation, strong intermolecular hydrogen bonding and π-π stacking.

Notably, pBTABQ also displays considerable absorption in mid-infrared region (MIR) due to its extended aromatic core and correspondingly large dispersion of electronic bands, indicating excellent electronic delocalization.

BTABQ and pBTABQ exhibit intrinsic bulk electrical conductivities of $2.4\times10^{-5}$ S $cm^{-1}$ and $0.79\times10^{-6}$ S $cm^{-1}$ at room temperature, respectively. Electron paramagnetic resonance (EPR) spectra exhibit intense isotropic signals for organic radicals in both materials, and pBTABQ shows significantly higher signal intensity than BTABQ. Together with the intense Drude-type background MIR absorption, as revealed by diffuse-reflectance infrared Fourier transform spectroscopy (DRIFTS), pBTABQ has higher free carrier concentration. Overall, the incorporation of dense redox sites in extended conjugated structures with efficient electronic delocalization makes BTABQ and pBTABQ promising candidates for high-rate EES.

Example 2

The following example describes the electrochemistry of systems utilizing materials comprising BTABQ molecules and pBTABQ in neutral electrolytes.

Figure 12:
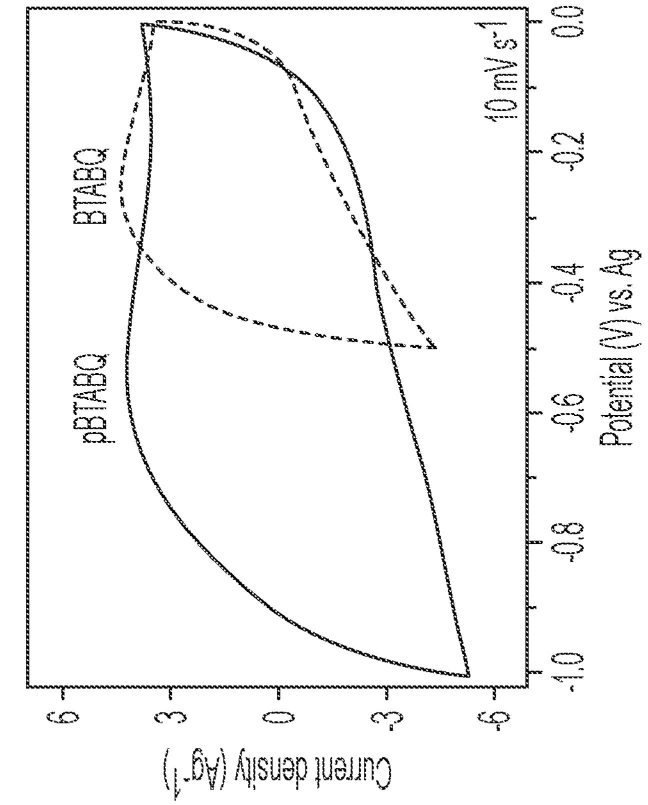
FIG. 12 shows, according to certain embodiments, cyclic voltammograms (CVs) of BTABQ and pBTABQ obtained at a scan rate of 10 mV $s^{-1}$ using 1 M LiCl aqueous electrolyte.
Figure 13:
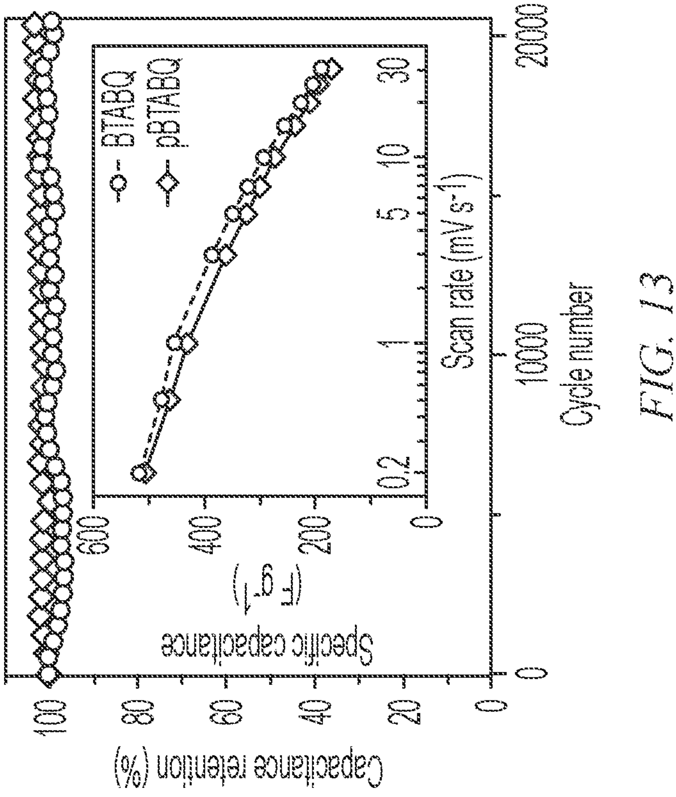
FIG. 13 shows, according to certain embodiments, a plot of capacitance retention as a function of CV cycle number for BTABQ and pBTABQ, wherein the inset shows gravimetric specific capacitances as a function of scan rate.

Cyclic voltammograms (CVs) of BTABQ and pBTABQ, obtained in a three-electrode configuration using 1 M LiCl aqueous electrolyte, display quasi-rectangular curves at scan rates ranging from 0.2 to 30 mV $s^{-1}$ (FIG. 12). BTABQ and pBTABQ display stable currents in a reductive potential window of 0.5 V and 1.0 V, respectively. An analysis of the CV currents (i) at different scan rates (v) using the power law equation (i=avb) reveals b values close to unity for both materials, indicating that the charge-storage processes are not limited by ion diffusion. Altogether, electrochemical behaviors of BTABQ and pBTABQ are uniquely different from sharp redox features and diffusion-controlled behaviors generally observed for organic molecules with carbonyl or imine groups. Instead, these features resemble the behaviors reported for inorganic materials such as $RuO_2 \cdot nH_2O$ and MXenes that are capacitor-like but exhibit a rapid redox-based charge storage mechanism, pseudocapacitance. Indeed, both BTABQ and pBTABQ have low specific surface areas (<20 $m^2$ $g^{-1}$), but exhibit high gravimetric specific capacitances, calculated from the CVs, of ~510 F $g^{-1}$ at 0.2 mV $s^{-1}$ and ~300 F $g^{-1}$ at 10 mV $s^{-1}$ (FIG. 13, inset), indicating a possibility of pseudocapacitive charge storage mechanisms. Galvanostatic charge-discharge (GCD) experiments at current densities ranging from 2 to 10 Å $g^{-1}$ display triangular voltage vs. time profiles and confirm their high capacitances. Additionally, both materials display excellent retention of capacitance over 20000 cycles in CVs at a high scan rate of 30 mV $s^{-1}$ (FIG. 13) and in GCD experiments at a current density of 10 Å $g^{-1}$.

Figure 14:
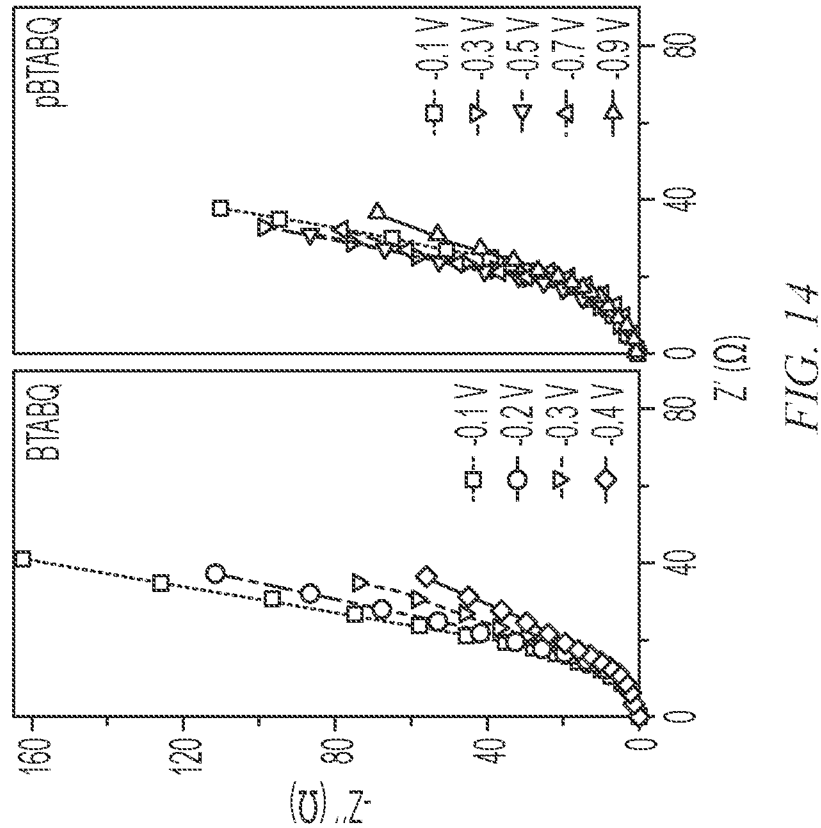
FIG. 14 shows, according to certain embodiments, electrochemical impedance spectra of BTABQ and pBTABQ.

The observed charge-storage behavior was further evaluated under dynamic conditions through electrochemical impedance spectra (EIS) at various negative potentials. Nyquist plots of impedance for both BTABQ and pBTABQ (FIG. 14) display typical capacitor-like features with low equivalent series resistances (~1-2Ω), short semicircles and 45° transition regions along with an extended 90° capacitive region at low frequencies. Meanwhile, semicircles in the high frequency region reveal decreasing diameters with applied negative potentials, confirming that fast charge transfer events happen during charge storage of both materials. Overall, EIS and CVs of BTABQ and pBTABQ display capacitor-like features and highlight a possibility of pseudocapacitive charge-storage mechanism.

Redox processes during charge storage were analyzed through ex-situ X-ray photoelectron spectroscopy (XPS) and solid-state nuclear magnetic resonance (ssNMR) studies of pristine and negatively polarized electrodes. The amino functional groups in pristine BTABQ and pBTABQ have partial imine character due to keto-enol tautomerization, as verified by the imine carbon chemical shift at 146.4 ppm in ssNMR of BTABQ, and N 1 s XPS spectra of both materials. Deconvolution of O 1s XPS spectra of polarized electrodes reveal a significant decrease in the intensity of C═O peak and the appearance of a C—$O^-$ peak, indicating the reduction of carbonyl groups. Deconvolution of N 1s spectra indicates the disappearance of imine component and growth of benzoid-amine component upon reduction. ssNMR of polarized BTABQ further supports that both carbonyl and imine groups are the redox-active sites for charge-storage in BTABQ and pBTABQ. Charges stored at these redox sites are delocalized both intramolecularly within the fused aromatic backbones, and intermolecularly through hydrogen bonding and D-A π-π stacking, manifesting in distinctly quasi-rectangular CVs. In contrast, small organic molecules with localized electronic structures display well-defined and sharp redox features. Moreover, larger π-conjugated organic molecules with close π-π stacking, such as 5,7,12,14-pentacetetrone, that lack hydrogen bonding interactions also exhibit limited electronic delocalization, leading to sharp, well-separated redox peaks in its CVs.

Figure 16:
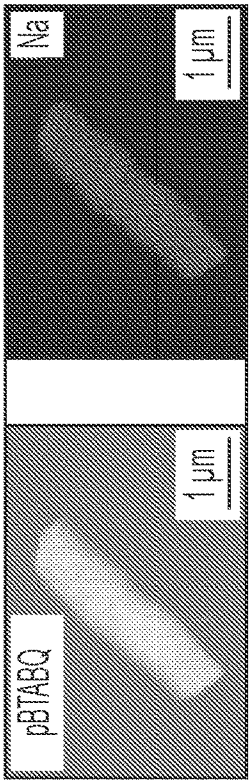
FIG. 16 shows, according to certain embodiments, ex-situ energy dispersive spectroscopy (EDS) mapping of pBTABQ.
Figure 15:
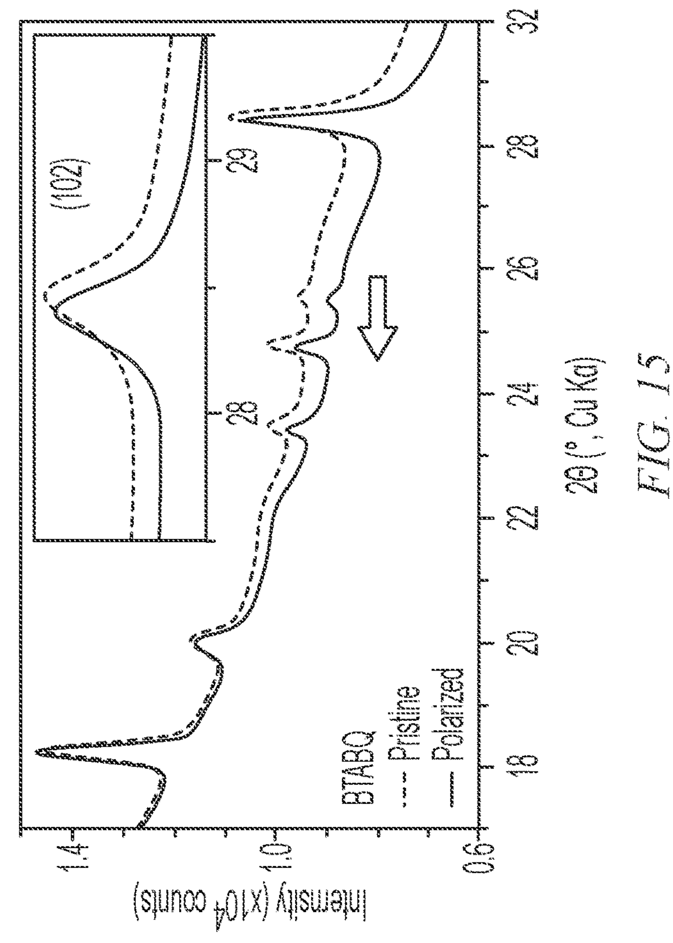
FIG. 15 shows, according to certain embodiments, in-situ wide-angle X-ray scattering (WAXS) patterns of pristine and negatively polarized BTABQ.

The nature of pseudocapacitance in BTABQ and pBTABQ, whether as a surface-confined or an intercalation-based bulk process, was probed through spectroscopic studies. In-situ wide-angle X-ray scattering (WAXS) patterns of negatively polarized BTABQ display a notable shift of (102) reflection toward a lower 2θ value (FIG. 15). This increase in spacing between 2D layers of BTABQ during $Li^+$ insertion supports an intercalation-based charge storage mechanism. Remarkably, other cations such as $Na^+$ and $Mg^{2+}$ can also intercalate into both materials, as verified by ex-situ energy dispersive X-ray spectroscopy (EDS) studies of polarized samples (FIG. 16). Elemental mapping indicates that significant amount of metal cations uniformly distribute throughout the particles, highlighting charge storage in the bulk of both BTABQ and pBTABQ electrodes.

Figure 18:
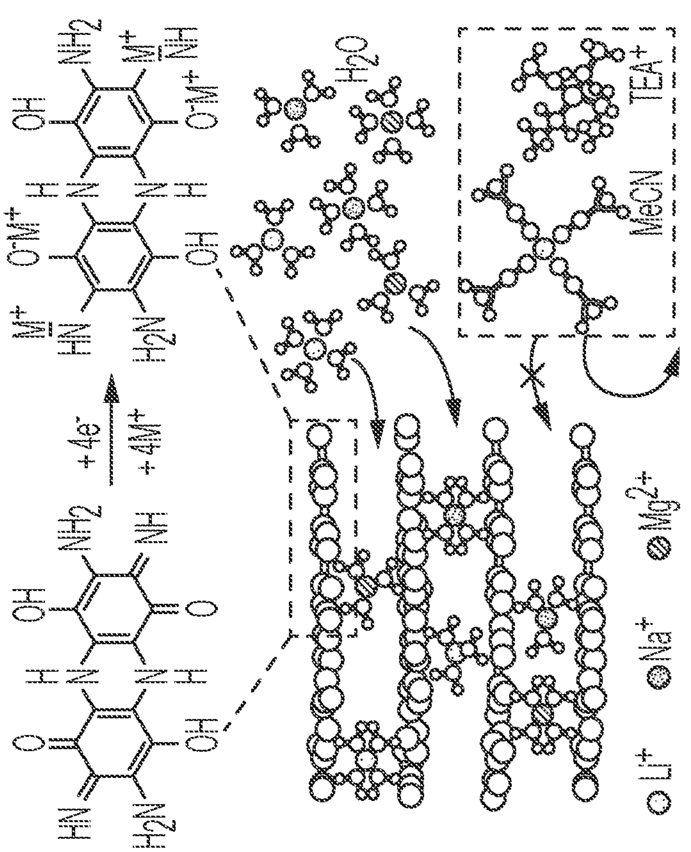
FIG. 18 shows, according to certain embodiments, a schematic representation of water-assisted pseudocapacitive intercalation of cations into BTABQ.

A comprehensive understanding of the role of electrolytic ions and solvents on intercalation was sought through electrochemical studies in a variety of electrolytes. Both materials show largely similar CVs in different alkali or alkaline earth electrolytes. However, markedly lower currents in CVs were obtained using electrolytes containing tetraethylammonium ($TEA^+$) cations. Replacing $TEA^+$ with an increasing amount of $Li^+$ resulted in an increase in CV currents. Altogether, these results indicate that both materials can intercalate a variety alkali and alkaline earth ions but exclude larger $TEA^+$ ions (FIG. 18). This ability of BTABQ and pBTABQ to intercalate multiple cations and display a size-based sieving behavior is similar to the reported behavior of MXenes and coordination polymers that exhibit intercalation pseudocapacitance.

Figure 17:
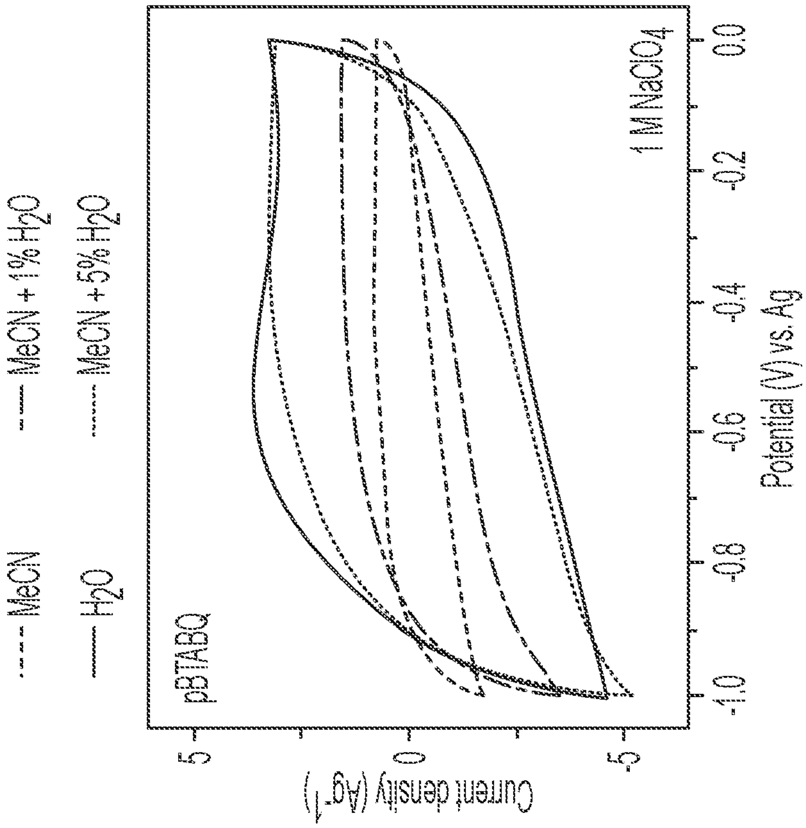
FIG. 17 shows, according to certain embodiments, CVs of pBTABQ recorded in electrolytes containing 1 M $NaClO_4$ in mixtures of water and acetonitrile.

The role of solvent on intercalation was probed through CVs in organic and aqueous electrolytes. CVs of pBTABQ recorded in 1 M sodium perchlorate ($NaClO_4$) solution of acetonitrile (MeCN) exhibit substantially lower currents than that recorded under aqueous conditions (FIG. 17). Adding 1% or 5% water to MeCN lead to significant increments in observed currents. However, similar enhancement was not observed when adding water to electrolytes containing $TEA^+$. These results suggest an important role of water during cation intercalation into BTABQ and pBTABQ. Specifically, water can act as a co-intercalant that facilitates intercalation and diffusion of metal cations without causing significant structural distortion of electrode materials, analogous to water-assisted intercalation of metal cations into vanadium oxides and Prussian blue analogues (PBAs). The co-intercalation of water molecules, likely as part of the hydration spheres of intercalating cations (FIG. 18), is promoted by the hydrogen bonding networks in BTABQ and pBTABQ, which may also enhance the total amount of stored charge.

Example 3

The following example describes the influence of pH on charge storage of systems utilizing materials comprising BTABQ molecules and pBTABQ.

Electrolyte pH has been shown to strongly influence the charge-storage behavior of pseudocapacitive materials. Considering the strong role of hydrogen bonding and water co-intercalation in BTABQ and pBTABQ, the influence of pH on their electrochemical behavior using aqueous NaCl electrolytes with a wide pH range of 0 to 14.7 was evaluated. While both materials exhibit similar pH dependent behavior, the following discussion is primarily focused on pBTABQ considering its larger electrochemical window (1 V).

Figure 20:
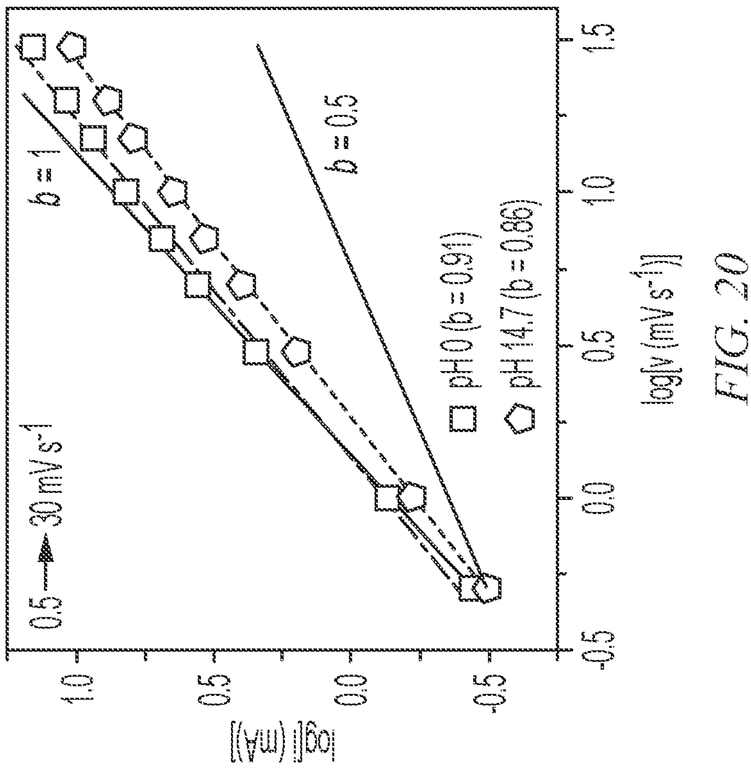
FIG. 20 shows, according to certain embodiments, a plot of peak current as a function of scan rate.
Figure 19:
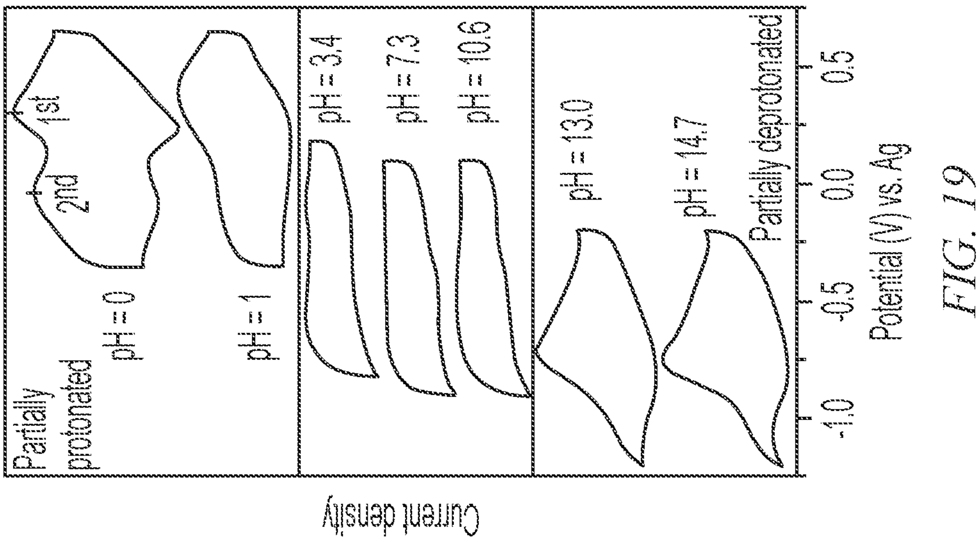
FIG. 19 shows, according to certain embodiments, CVs obtained at a 5 mV $s^{-1}$ scan rate in several 1 M NaCl electrolytes adjusted with pH values ranging from 0 to 14.7.
Figure 21:
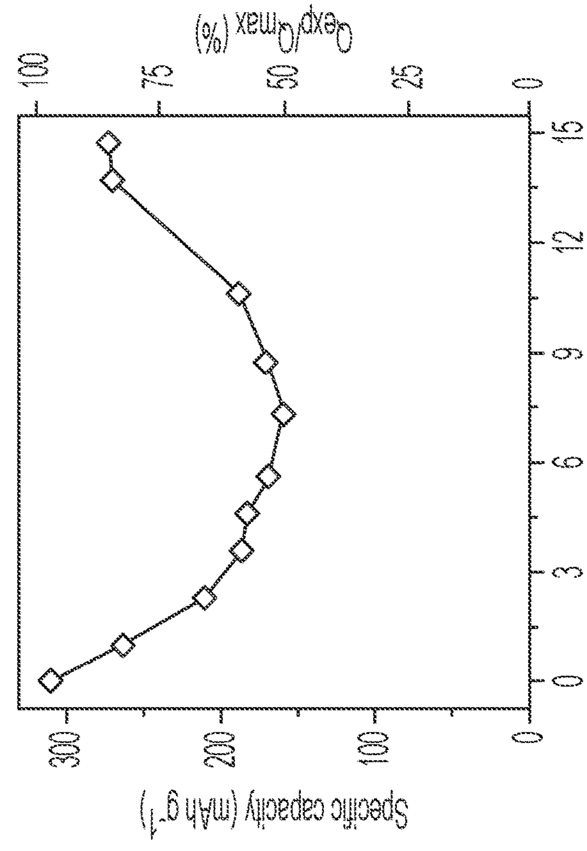
FIG. 21 shows, according to certain embodiments, a plot of gravimetric specific capacities as a function of electrolyte pH obtained from CVs at a scan rate of 0.2 mV $s^{-1}$.

CVs recorded in electrolytes with intermediate pHs remain quasi-rectangular, whereas CVs recorded under highly acidic and alkaline conditions exhibit broad redox features with small peak separations and markedly increased current densities (FIG. 19). Specifically, two sets of broad redox peaks are noted at pH of 0 and 1, whereas a single broad redox feature is observed at pH of 13 and 14.7. The aforementioned analysis of peak currents vs. scan rates finds b values of ~0.9 at low and high pHs (FIG. 20), indicating that the charge storage is still not limited by bulk ion diffusion. The total amount of charge stored at different pHs, calculated as gravimetric specific capacity (mAh $g^{-1}$) from CVs at 0.2 mV $s^{-1}$, increases from ~160 mAh $g^{-1}$ at intermediate pHs to 272 and 310 mAh $g^{-1}$ at pH of 14.7 and 0, respectively, displaying a U-shaped curve (FIG. 21). Such pH-dependence of specific capacities has previously been observed for $RuO_2 \cdot xH_2O$, but to our knowledge is the first instance in organic systems. Remarkably, the observed capacities are substantially higher than state-of-the-art inorganic LIC cathodes and pseudocapacitive electrodes that function at comparable electrochemical potentials. Moreover, high capacities of 225 mAh $g^{-1}$ (pH=0), 135 mAh $g^{-1}$ (pH=14.7), and 72 mAh $g^{-1}$ (pH=7.3) can be accessed within 33 seconds, indicating excellent rate capability. pBTABQ exhibits best rate capability at pH 0, with retention of 96%, 90% and 70% capacities relative to the highest capacity of 320 mAh $g^{-1}$ ($Q_{max}$, 0.05 mV $s^{-1}$), at increasing scan rates of 0.2, 5 and 100 mV $s^{-1}$, respectively. Alternatively, a 12-electron reduction of pBTABQ assigns a theoretical capacity of 389 mAh $g^{-1}$, indicating 82% experimental bulk utility of pBTABQ at pH 0. Further GCD tests at pH 0 using high current densities of 2-10 Å $g^{-1}$ also deliver capacities greater than 200 mAh $g^{-1}$ at rates corresponding to 6-50 C (1 C=discharge in 1 hour).

Figure 22:
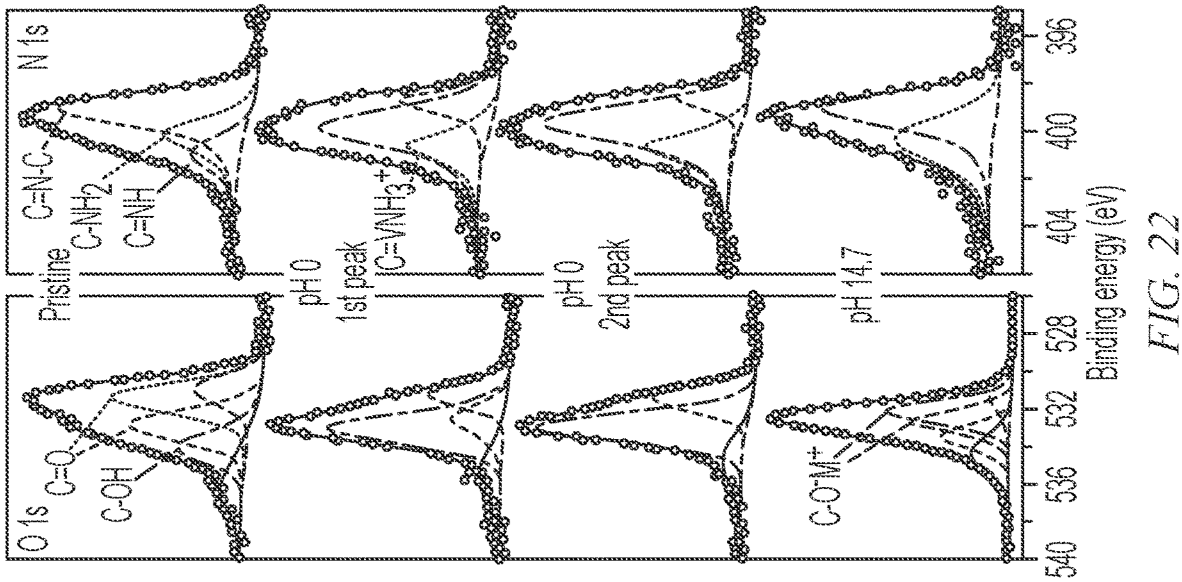
FIG. 22 shows, according to certain embodiments, ex-situ high resolution O 1s and N 1s X-ray photoelectron spectra of polarized electrodes.
Figure 23:
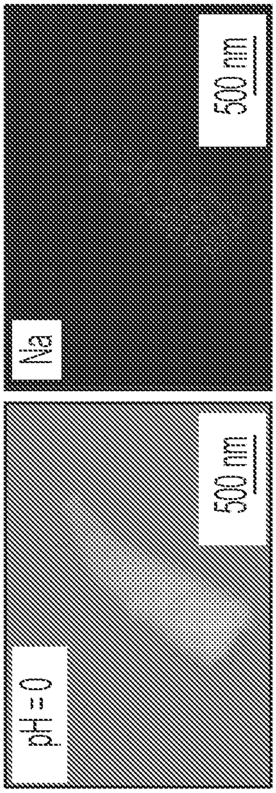
FIG. 23 shows, according to certain embodiments, EDS mappings of polarized pBTABQ under pH 0.
Figure 24:
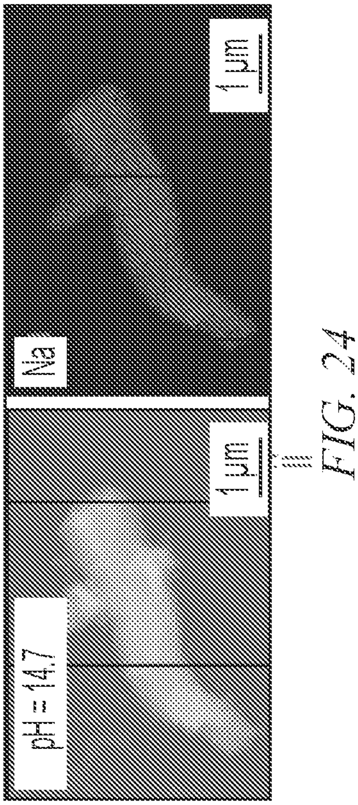
FIG. 24 shows, according to certain embodiments, EDS mappings of polarized pBTABQ under pH 14.7.
Figure 25:
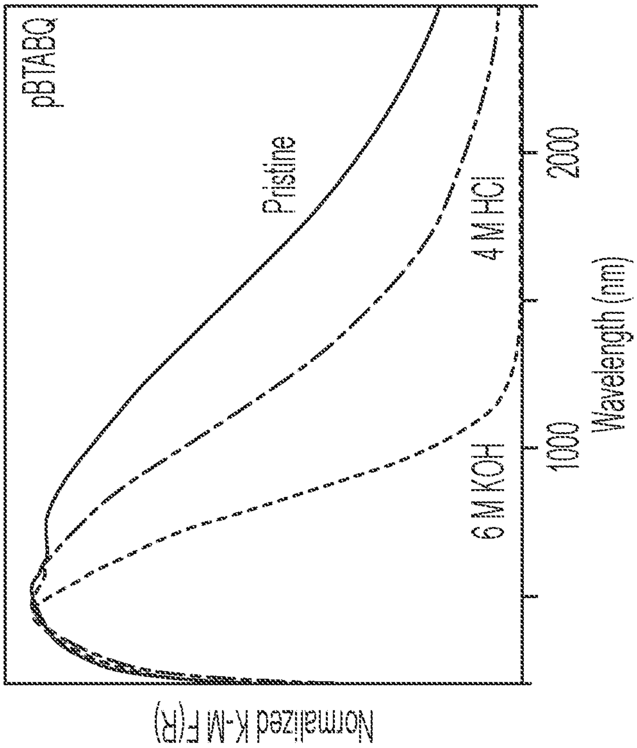
FIG. 25 shows, according to certain embodiments, DRUV-Vis spectra of pristine and soaked pBTABQ in 4 M HCl and 6 M KOH.

The emergence of high capacities and redox peaks under acidic and alkaline conditions was analyzed through ex-situ studies on polarized electrodes. Firstly, charge storage still occurs through the reduction of imines and carbonyls, as revealed by the decreasing intensity of O 1s (C═O) and N 1s (C═N) XPS signals upon polarization (FIG. 22). Notably, ion intercalation in highly acidic conditions occurs almost exclusively through protons, as evidenced by the absence of alkaline ions in XPS and elemental mapping (FIG. 23). Secondly, the emergence of broad redox peaks suggests localized redox states, likely due to the weakening of electronic delocalization by partial protonation or deprotonation of electrode materials under highly acidic or alkaline conditions. Indeed, the UV-Vis spectra of pBTABQ soaked in acid or base show significantly blue shifted absorption (FIG. 25), indicating more localized electronic structures. XPS analysis (FIG. 22) indicates that proton coupled electron transfer (PCET) occurs sequentially starting at both imines and carbonyls (pH 0 first peak) and then only at carbonyls (pH 0 second peak) under acidic conditions, whereas a broad reductive enolate formation dominates under alkaline conditions (pH 14.7). Remarkably, the selectivity of protons over metal cations highlights excellent bulk proton diffusion through the hydrogen bonding network of the electrode, leading to a superior charge storage throughout the electrode bulk. However, the contribution of PCET is likely very limited at highly basic conditions (pH>13), and cannot explain the considerable increase of specific capacity. Instead, substantially larger amount of $Na^+$ was observed in polarized pBTABQ under alkaline conditions than at neutral conditions (FIG. 24), indicating that the intercalation of metal cations into the electrode is significantly enhanced. This is likely due to hydrogen bonding assisted partial deprotonation of the bulk electrode materials by hydroxide ions at alkaline pH.

Example 4

The following example describes the charge-discharge capability of systems utilizing materials comprising BTABQ molecules and pBTABQ.

Figure 27:
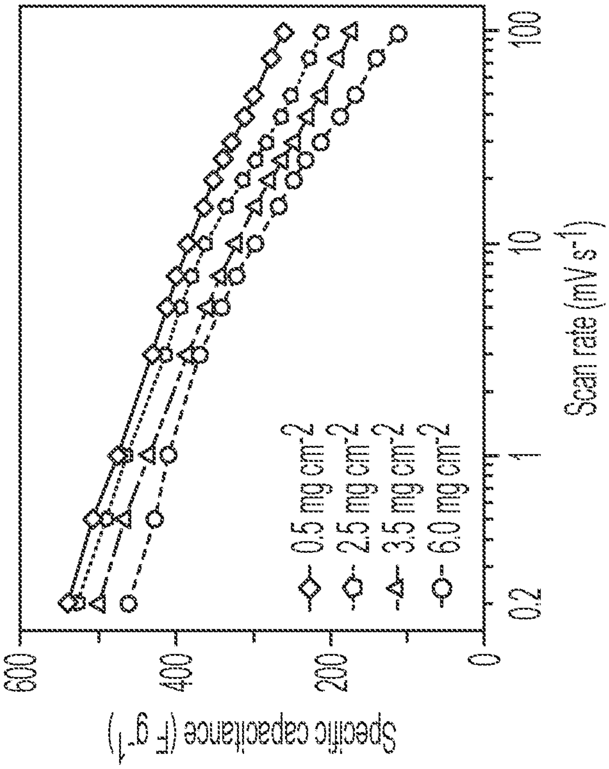
FIG. 27 shows, according to certain embodiments, the power performances of pBTABQ in WiSE obtained from CVs at scan rates ranging from 0.2 to 100 mV s 1 on electrodes with active material loadings of 1.5, 2.5, 3.5 and 6 mg cm 2.
Figure 26:
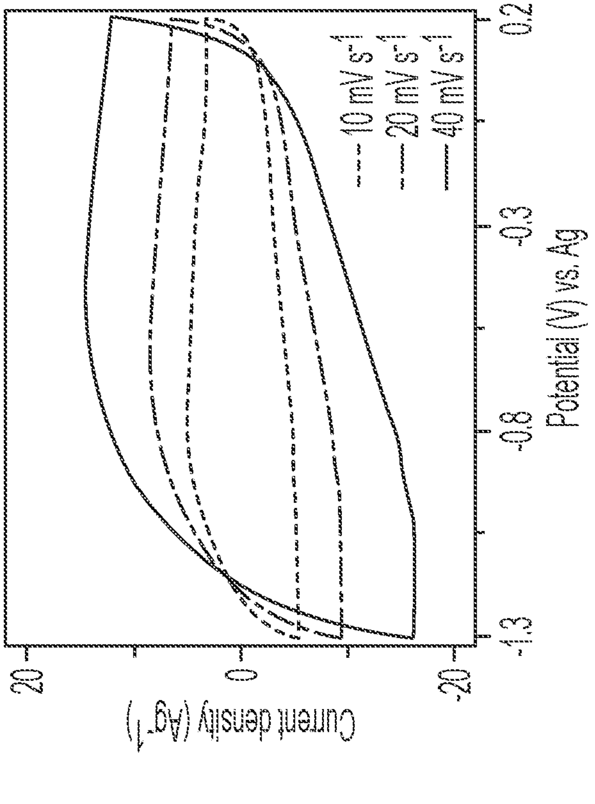
FIG. 26 shows, according to certain embodiments, CVs of pBTABQ obtained at 10, 20, and 40 mV $s^{-1}$ scan rates using 17 molal $NaClO_4$ water-in-salt electrolyte (WiSE)
Figure 28:
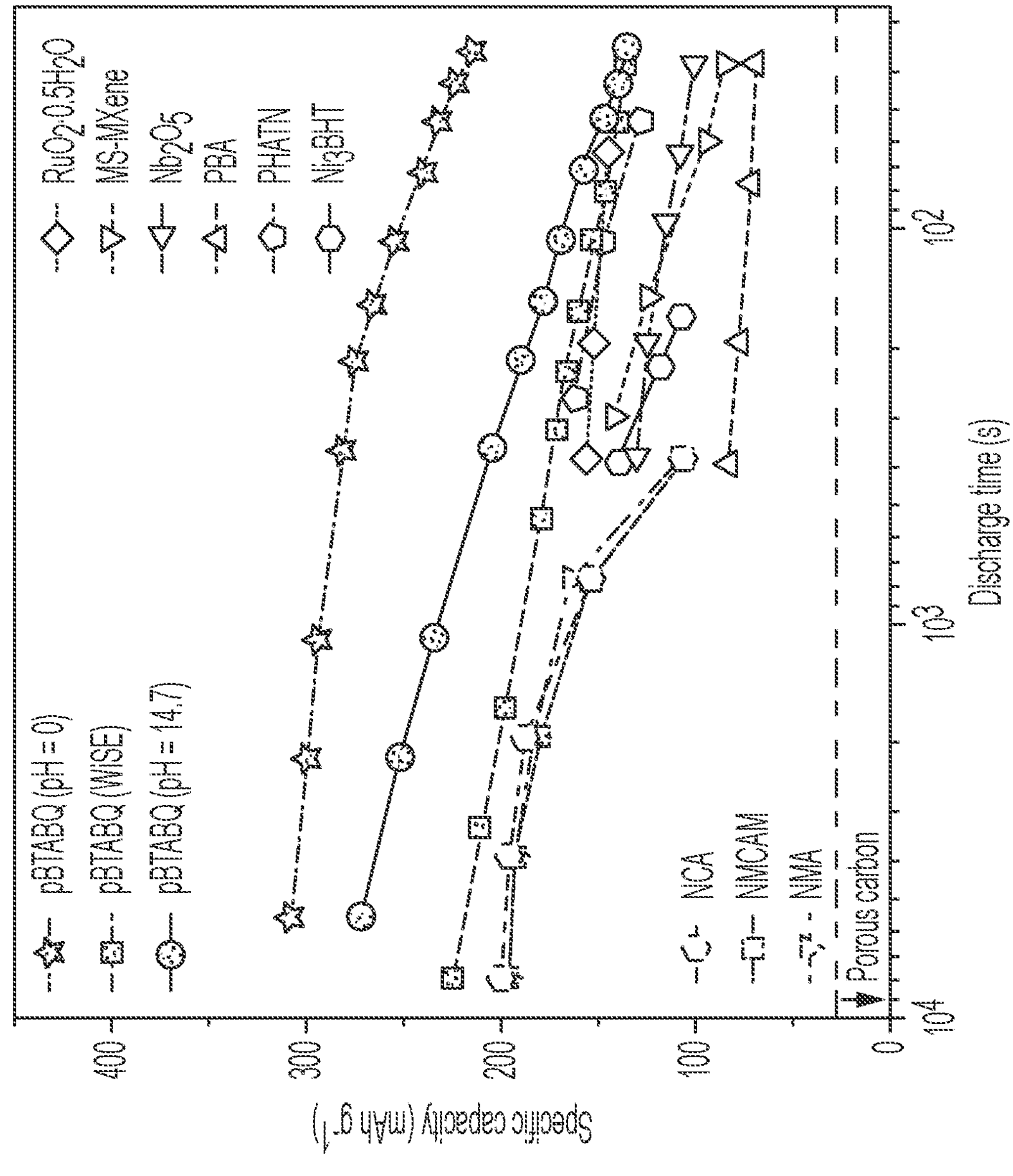
FIG. 28 shows, according to certain embodiments, a comparison of rate performances for pBTABQ and related state-of-the-art LIC cathodes and pseudocapacitive electrodes.

Benefiting from the recent development of water-in-salt electrolytes (WiSE), we explored deep charge-discharge capability of pBTABQ in a larger reductive potential window of 1.5 V. CVs recorded in 17 molal $NaClO_4$ remain quasi-rectangular, and deliver capacitances similar to those seen in aqueous neutral electrolytes with an excellent cyclic stability over 40000 cycles (FIG. 26). Notably, EDS maps of polarized pBTABQ electrode in WiSE reveal significantly larger amount of intercalated $Na^+$ relative to that observed in neutral electrolyte, indicating limited PCET contribution. Indeed, the capacitor-like behavior in CVs and EIS over an extended potential window in WiSE deliver high charge capacity of 225 mAh $g^{-1}$, a 50% increase relative to the neutral condition. Rate capability studies display ultrahigh-rate performances at various active material loadings up to practically relevant value of 6 mg $cm^{-2}$ (FIG. 27). For instance, discharge capacities greater than 100 mAh $g^{-1}$ can be delivered within 60 seconds. A summary of pBTABQ performances in acidic, alkaline and WiSE electrolytes highlights its predominance over state-of-the-art high-capacity LIC cathodes and high-rate pseudocapacitive electrodes (FIG. 28). Materials tested at potentials greater than 2 V vs. $Li^+/Li$ and with a minimum active material loading of 1.5 mg cm 2 were chosen for comparison (MS-Mxene: $Ti_3C_2T_x$ synthesized using Molten alkali salts, PHATN: perylene diimide-hexaazatrinaphthylene, NCA, NMCAM and NMA: Ni-rich analogues of $LiNiO_2$ doped with Al, Mn, Co and Mg, $Ni_3BHT$: $Ni_3$(benzenchexathiol)). An asymmetric hybrid capacitor fabricated using pBTABQ as the negative electrode and porous activated carbon as the positive electrode delivers 2 V and cycles safely over 60000 cycles with a capacitance retention over 90%. A careful selection of WiSE electrolyte can further enhance the cell voltage to 2.3 V. Overall, the fundamental understanding and design principles of organic pseudocapacitive materials here represent an essential step toward practical, high-rate, high-capacity EES devices.

Example 5

The following example describes the materials and methods used to synthesize and characterize materials comprising BTABQ molecules and pBTABQ.

Synthesis of BTABQ: To a 15 mL pressure tube (ACE Glass, 150 psi) with 28.4 mg of tetraamino-p-benzoquinone (TABQ, synthesized using a previously reported procedure) and 220 mg of tetrabutylammonium chloride (TBACl, TCI) was added 6 mL of dimethylformamide (DMF, Sigma-Aldrich). The tube was capped under ambient condition, sonicated for 1 minute, and then put into an isothermal oven at 120° C. After 12 hours, the tube was cooled down to room temperature, and the reaction mixture was filtered and washed with DMF until the filtrate coming out became colorless. The resulting black solid was further washed with methanol (Sigma-Aldrich) and dried under air. 15.5 mg of BTABQ was obtained (60% yield). BTABQ is insoluble in common NMR solvents. Solid-state NMR of BTABQ: 174.8 ppm (C═O), 146.4 ppm (C═N), 134.5 ppm/129.9 ppm (C—N/C—O). Elemental analysis: $C_{12}H_{10}O_4N_6$, found: C, 47.14%; H, 2.84%; N, 26.06%; calculated: C, 47.69%; H, 3.33%; N, 27.81%. MALDI-TOF: $[M+H]^+$: found, 303.9; calculated: 303.1; within the ±1 Da error of the instrument. The crystallinity of BTABQ was characterized by PXRD.

The synthesis of BTABQ can be scaled-up to gram scale: To a 250 mL Schlenk tube (ChemGlass) with 1.07 g of TABQ and 10.3 g of tetrabutylammonium bromide (TBABr, Sigma-Aldrich) was added 80 mL of dimethylformamide (DMF, Sigma-Aldrich). The Schlenk tube was sealed under ambient condition, sonicated for 1 minute, and then put into an isothermal oven at 120° C. After 12 hours, the Schlenk tube was cooled down to room temperature, and the reaction mixture was filtered and washed with DMF until the filtrate coming out became colorless. The resulting black solid was further washed with methanol (Sigma-Aldrich) and dried under air. 0.4 g of BTABQ was obtained (42% yield).

Synthesis of pBTABQ: 100 mg of BTABQ was transferred into a glass tube, heated at ~300° C. under vacuum for 2 days. 85 mg of pBTABQ was obtained as black solid. Elemental analysis: $C_{36}H_{10}O_{10}N_{16}$, found: C, 52.48%; H, 1.44%; N, 26.34%; calculated: C, 52.31%; H, 1.22%; N, 27.11%. MALDI-TOF: $[M+H]^+$: found, 827.7; calculated: 827.1; $[(M-NH_3)+H]^+$: found, 810.7; calculated: 810.1; within the ±1 Da error of the instrument.

Fabrication of electrodes: The working electrodes were fabricated as a slurry by mixing active materials, polyvinylidene fluoride (PVDF), and acetylene black carbon in a ratio of 8:1:1 using dimethylformamide and were coated onto 0.3 $cm^2$ carbon fibre paper disk (Fuel Cell Earth). The as prepared electrodes were dried at 65° C. in air for 3 hours prior to drying under vacuum at 120° C. overnight. The dried electrodes have loading densities of 1.5~6 mg/$cm^2$.

The activated carbon counter electrodes were prepared as thin films by repeated kneading and rolling of a slurry of activated carbon, acetylene black and a PTFE solution mixture, in a ratio of 8:1:1, with ethanol. The prepared films were dried at 120° C. overnight prior to use.

Preparation of electrolytes: Electrochemical tests in neutral conditions were performed using 1 M aqueous solutions of LiCl, NaCl, $MgCl_2$, tetraethylammonium chloride (TEACl) in deionized water. Detailed studies aimed at probing the role of water were performed using 1 M solutions of $NaClO_4$ and tertraethylammonium tetrafluoroborate ($TEABF_4$) in pure water, anhydrous acetonitrile (MeCN) and solution mixtures of 1% and 5% water in MeCN.

The role of pH on electrochemical performances was probed using electrolytes with pH values ranging from 0 to 14.7. Electrolytes with intermediate pH values between 2 and 13 were buffered whereas, highly acidic and basic solutions were unbuffered. While 1 M NaCl was used to maintain comparable ionic strengths, HCl and NaOH were used to adjust the pH of buffered solutions. A description of electrolytes and their constituents are shown in Table 1.

TABLE 1

Electrolytes and their constituents.

| Electrolyte pH | Electrolyte constituents |
|---|---|
| 0 | 1M HCl + 1M NaCl |
| 1 | 0.1M HCl + 1M NaCl |
| 2.6 | 89 mL 0.1M Citric acid + 11 mL 0.2M $Na_2HPO_4$ + 1M NaCl |
| 3.4 | 71 mL 0.1M Citric acid + 29 mL 0.2M $Na_2HPO_4$ + 1M NaCl |
| 4.5 | 53 mL 0.1M Citric acid + 47 mL 0.2M $Na_2HPO_4$ + 1M NaCl |
| 5.4 | 44 mL 0.1M Citric acid + 56 mL 0.2M $Na_2HPO_4$ + 1M NaCl |
| 7.3 | 9 mL 0.1M Citric acid + 91 mL 0.2M $Na_2HPO_4$ + 1M NaCl |
| 9.0 | 10 mL 0.1M $Na_2CO_3$ + 90 mL 0.1M $Na_2HCO_3$ + 1M NaCl |
| 10.6 | 90 mL 0.1M $Na_2CO_3$ + 10 mL 0.1M $Na_2HCO_3$ + 1M NaCl |
| 13 | 0.1M NaOH + 1M NaCl |
| 14.7 | 6M NaOH + 1M NaCl |

Deep charge-discharge tests in water-in-salt electrolytes (WiSE) were done using 17 m (molality) $NaClO_4$ in three-electrode configuration. Two electrode devices were fabricated using WiSE containing 12.5 m $LiNO_3$ in 1:1 weight ratio of water and 1,5-pentanediol.

In house powder X-ray diffraction (PXRD) patterns were recorded using a Bruker Advance II diffractometer equipped with a θ/2θ reflection geometry and Ni-filtered Cu Kα radiation ($K\alpha_1$=1.5406 Å, $K\alpha_2$=1.5444 Å, $K\alpha_2/K\alpha_1$=0.5). The tube voltage and current were 40 kV and 40 mA, respectively. Samples for PXRD were prepared by placing a thin layer of the appropriate material on a zero-background silicon crystal plate.

For cRED data collection, procession, and structure solution of BTABQ, crystals were dispersed in ethanol and ultrasonication for 5 minutes. A droplet of suspension was then transferred on a copper grid with carbon film. The cRED data were collected on 200 kV JEOL JEM-2100 transmission electron microscope equipped with a quad hybrid pixel detector (Timepix, 512×512 pixels, pixel size 55 μm, Amsterdam Sci. Ins.). Before data collection, the sample was cooled down to 96 K by using Gatan cryo-transfer tomography holder. During data collection, the goniometer was rotated continuously while the selected area electron diffraction (ED) patterns were captured from the crystal simultaneous by using the software of instamatic. In order to balance the intensity of electron diffraction and resolution, all the ED patterns were recorded under the spot size 3 with the exposure time 0.5 s. The 3D reciprocal lattice was reconstructed by the software REDp, which was very useful for indexing and obtaining the reflection conditions.

For the structure solution of BTABQ, five crystals could be indexed with orthorhombic symmetry, with mean lattice parameters of a=Å, b=Å, c=Å in space group (reflection condition: hk0, h+k=2n, h0l, h=2n, 0k0, k=2n). The X-ray crystallography software package XDS was used for data processing to estimate integrated diffraction intensities. In order to improve the completeness, XSCALE was then applied for data merging, which resulted in a completeness of 88.9% by merging the five datasets. The SHELX software package was used for structural analysis, where SHELXT was used for structure solution. As the resolution of these cRED datasets was measured up to 0.625 Å, all non-hydrogen atomic positions in BTABQ can be located directly by an ab initial method. The SHELXL was used for structure refinement using electron scattering factors for all the atoms. The atomic displacement parameters (ADPs) for all framework atoms were refined anisotropically.

High-resolution synchrotron PXRD data were collected at 100 K in the beamline 11-BM at the Advanced Photon Source (APS), Argonne National Laboratory using the Debye-Scherrer geometry and an average calibrated wavelength of 0.458111 Å.

Pawley refinement of synchrotron data of BTABQ was conducted using TOPAS Academic (version 6). The refined lattice parameters of BTABQ at 100 K are a=4.8923(1) Å, b=11.2897(3) Å, c=9.9041(4) Å, B=101.67° in the space group $P2_1/c$, with $R_{wp}$=5.828, $R_{exp}$=5.248, $R_p$=4.667, and GoF=1.11.

$N_2$ adsorption isotherms were measured by a volumetric method using a Micromeritics ASAP 2020 Plus gas sorption analyzer. An oven-dried sample tube equipped with a TranSeal™ (Micromeritics) was evacuated and tared. The sample was transferred to the sample tube, which was then capped with a TranSeal™. The sample was activated at 100° C. under high dynamic vacuum (<$10^{-4}$ mbar) for 24 hours before analysis. The $N_2$ isotherm was measured using a liquid nitrogen bath at 77 K. Ultrahigh purity grade (99.999% purity) $N_2$, oil-free valves and gas regulators were used for all the free space correction and measurements. Fits to the Brunauer-Emmett-Teller (BET) equation satisfied the published consistency criteria.

Thermogravimetric analysis (TGA) was performed on a TA Instruments Q500 Thermogravimetric Analyzer at a heating rate of 2.0° C./min under air or $N_2$ gas flow of 5 mL/min on a platinum pan from room temperature to 700° C.

Elemental analyses were performed by Robertson Microlit Laboratories, Ledgewood, New Jersey.

X-ray photoelectron spectroscopy (XPS) measurements were performed at the MIT MRSEC (formerly the Center for Materials Science and Engineering, or CMSE) using a Physical Electronics PHI Versaprobe II X-ray photoelectron spectrometer equipped with a monochromatic Al anode X-ray source. The main chamber pressure was in the $10^{-10}$ Torr range. MOF powder samples were pressed on copper tapes with full coverage. Survey spectra were collected from 0~1100 eV in binding energy (BE), with a resolution of 0.8 eV. High resolution spectra of C1 s, N1 s, and M2p regions were collected with a resolution of 0.1 eV. BE calibration was carried out by shifting the adventitious carbon C1s peak to 284.8 eV. Deconvolution of the C1s spectra were conducted before BE calibration to find out the adventitious carbon C1s peak, given that the MOF samples also contain significant amount of carbon. Gaussian-Lorentzian product function with 30% of Lorentzian component was used for the line shapes during fitting, which is commonly used for C1 s.

Scanning electron microscopy (SEM) was conducted at MIT MRSEC (formerly the Center for Materials Science and Engineering, or CMSE) on a Zeiss Merlin high-resolution scanning electron microscope with an InLens detector at an operating voltage of 3 or 4 kV.

MALDI-TOF mass spectrometry was conducted using a high-resolution Bruker Autoflex LRF Speed mass spectrometer in the positive linear mode. Dithranol was used as the Matrix. Powder samples were mixed with dithranol using mortar and pestle, and the mixtures were pressed into pellets for the measurements. No internal standards were used; therefore, the mass accuracy is ±1 Da.

Cryo-HRTEM images were obtained at the Automated Cryogenic Electron Microscopy Facility in MIT.nano on a Talos Arctica G2 microscope operated at an accelerating voltage of 200 kV with a Falcon3EC direct electron detector. Samples were prepared by sonicating powders in isopropanol for ~5 seconds. Specimens were prepared by drop-casting sonicated samples onto C-Flat™ Cu grids with holey carbon for Cryo-EM. All image acquisition was done using EPU at an exposure time of 1 s, with focusing done adjacent to the region imaged to minimize beam exposure prior to image acquisition (standard low dose imaging protocols). Analysis of the raw HRTEM data was done using Gatan Microscopy Suite software (GMS 3).

Diffuse reflectance infrared Fourier transform spectroscopy (DRIFTS) was performed on a Bruker Tensor 37 (MIR source and KBr beam splitter) with a mercury cadmium telluride (MCT, cooled with $LN_2$) detector utilizing the DiffusIR™ accessory (Pike Technologies). To ensure air-free measurement, a scalable environmental chamber equipped with ZnSe window (Pike Technologies) was used. Samples were ground in air with dry KBr (99.9%, Pike technologies) in a mortar and pestle to produce 0.5-1% wt. mixtures. The data was averaged over 64 scans between 4000-600 $cm^{-1}$ with the resolution of 4 $cm^{-1}$. Each of the Kubelka-Munk function transformed DRIFTS spectra were normalized with respect to the DRUV-vis-NIR data by matching the DRIFTS value of F(R) at 4000 $cm^{-1}$ with the DRUV-vis-NIR value of F(R) of the same sample at 4000 $cm^{-1}$.

Diffuse reflectance UV-Vis-NIR spectra (DRUV-Vis-NIR) between 200 and 2500 nm were collected on a Cary 5000i spectrophotometer, fitted with the UV-Vis DiffusIR accessory (Pike Technologies), at the scan rate of 600 nm/min under ambient conditions. A KBr baseline and a zero-background correction were collected prior to the sample measurements. Samples were prepared as described above for the DRIFTS measurements. For the Tauc plots and the determination of the optical bandgaps, the UV-Vis-NIR spectra were stitched manually with the DRIFTS spectra obtained for the same samples.

Raman spectra of solid samples were measured using a Renishaw Invia Reflex Raman Confocal Microscope under the excitation laser of 532 nm, with the laser not exceeding 5% of the full power.

Room temperature electrical conductivity measurements were carried out at 294 K in ambient atmosphere on pressed pellets using a 4-probe probe setup described previously. For each sample, the conductivity values were averaged among at least 3 devices.

Electron paramagnetic resonance spectroscopy (EPR) measurements were performed on activated samples packed under nitrogen in septum-sealed quartz tubes using a Bruker EMX spectrometer equipped with an ER 4199HS cavity and Gunn diode microwave source at ~5 K, with a microwave frequency of 9.37 GHZ, power of 0.100 mW, and attenuation of 33.0 dB. The measurements were taken in perpendicular mode. Pure MOF and CCP powder samples were used for the measurements.

The in-situ wide-angle X-ray scattering (WAXS) measurements were conducted at the Soft Matter Interfaces beamline (12-ID) of the National Synchrotron Light Source II (NSLS-II) at Brookhaven National Laboratory with a beam energy of 16.1 keV and beam size of 200× 20 μm. The coin cells were connected to the Princeton Applied Research Potentiostat (PARSTAT 2273) for in-situ bias controlling through metal wires. A home-made 3D printed holder was used to load the coin cell samples on the sample stage for transmission WAXS studies, ensuring that the cells were in the line of the beam. The Scattered data were collected in a vacuum with a PILATUS3 300 kW detector (Dectris, Switzerland), consisting of 0.172 mm square pixels in a 1475× 195 array. To obtain a wide range of wave vector transfer (q), a series of 2D diffraction patterns were collected by rotating the detector on an arc with the sample-to-detector distance being 275 mm. Scattering patterns from each detector angle were stitched together using custom software and then reduced to 1D scattering intensity versus q curve by circular average. In-situ cells for WAXS were designed by machining commercial CR 2032 Coin cells. Specifically, a hole with a diameter of 3 mm was drilled into the top and bottom casings of the Coin cells. The holes were capped with a piece of Kapton tape and sealed with epoxy to facilitate transmission of X-rays and prevent electrolyte from leaking. Similar holes were also made in the separator and the porous carbon counter electrode. All cell components were arranged carefully into a stack to ensure a seamless transmission of X-ray beam through the BTABQ pellet. The fabricated cells were tested for their electrochemical performances using cyclic voltammetry prior to loading them in the WAXS chamber. Cells were tested at their corresponding rest potentials and then reversibly polarized to −0.9 V vs. OCP.

Ex-situ high-angle annular dark-field scanning transmission electron microscope (HAADF-STEM) images and energy dispersive spectroscopy elemental mapping were collected at the MIT MRSEC (formerly the Center for Materials Science and Engineering, or CMSE) on a JEOL 2010 FEG Analytical Electron Microscope equipped with an Oxford Instrument ULTIM MAX detector. The specimens were prepared by drop-casting polarized samples onto Cu grids.

Electrochemical Characterization Methods: The synthesized materials were first tested in a three-electrode supercapacitor configuration with porous activated carbon (YP50) as counter, a silver wire as reference electrode, and a 25 μm thick cellulose sheet as a separator. Porous activated carbon electrodes with excess weight were used to counter the charges and ensure distinct responses from the working electrodes. A custom-built T-shape Swagelok type cell was used to assemble the cell components. Aqueous, organic, or aqueous/organic mixed solutions of various metal salts were used as electrolytes. Cells were assembled in a fume hood and allowed to rest for 12 hours before electrochemical tests.

All electrochemical measurements were carried out using a Biologic VSP-300 potentiostat controlled by the software EC-Lab. EIS measurements were performed using a multi-sinusoidal signal with an amplitude of 10 mV over a large frequency range of 10 mHz-200 kHz. The specific gravimetric capacitance ($C_g$) was calculated from the discharge sequence of three-electrode CV curves using Equation 1:

$$C_g = \left(\int (idv)\right) \Big/ (2mvdV) \qquad \text{(Equation 1)}$$

where m=mass of the working electrode, dV=discharge potential window, v=scan rate. CVs at different scan rates were compared by plotting their rate normalized currents: divide current by the corresponding scan rates.

Kinetics of the electrochemical processes were analyzed using the power law equation shown in Equation 2.

$$i(v) = av^b \qquad \text{(Equation 2)}$$

Plotting log (i) vs. log (n) allowed determination of b as the slope of the fit. Following this approach, b values were evaluated at various potentials on a CV over a range of scan rates using neutral, acidic and basic electrolytes.

Calculations of theoretical capacity: The theoretical capacity of a material is calculated by Faraday's law using Equation 3:

$$Q_{theoretical} = \frac{nF}{3.6 \times MW} \text{ mAh g}^{-1} \qquad \text{(Equation 3)}$$

where n is the number of electrons involved in the redox event, F is the Faraday constant 96485 s A $mol^{-1}$, and MW is the molecular weight of the material (g $mol^{-1}$).

Figure 29:
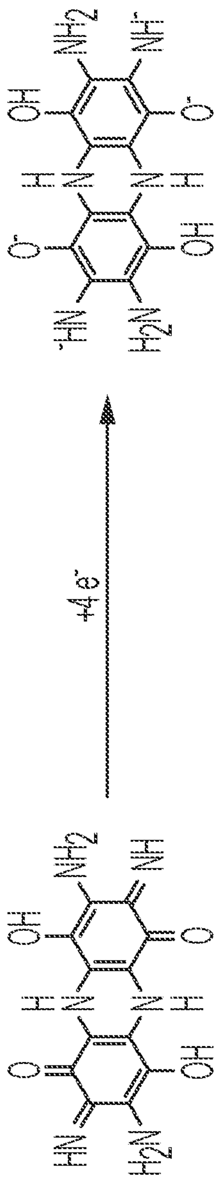
FIG. 29 shows, according to certain embodiments, a schematic representation of the 4-electron reduction of BTABQ.

For BTABQ, the theoretical capacity is calculated to be 355 mAh $g^{-1}$, based on the redox process shown in FIG. 29 (n=4).

Figure 30:
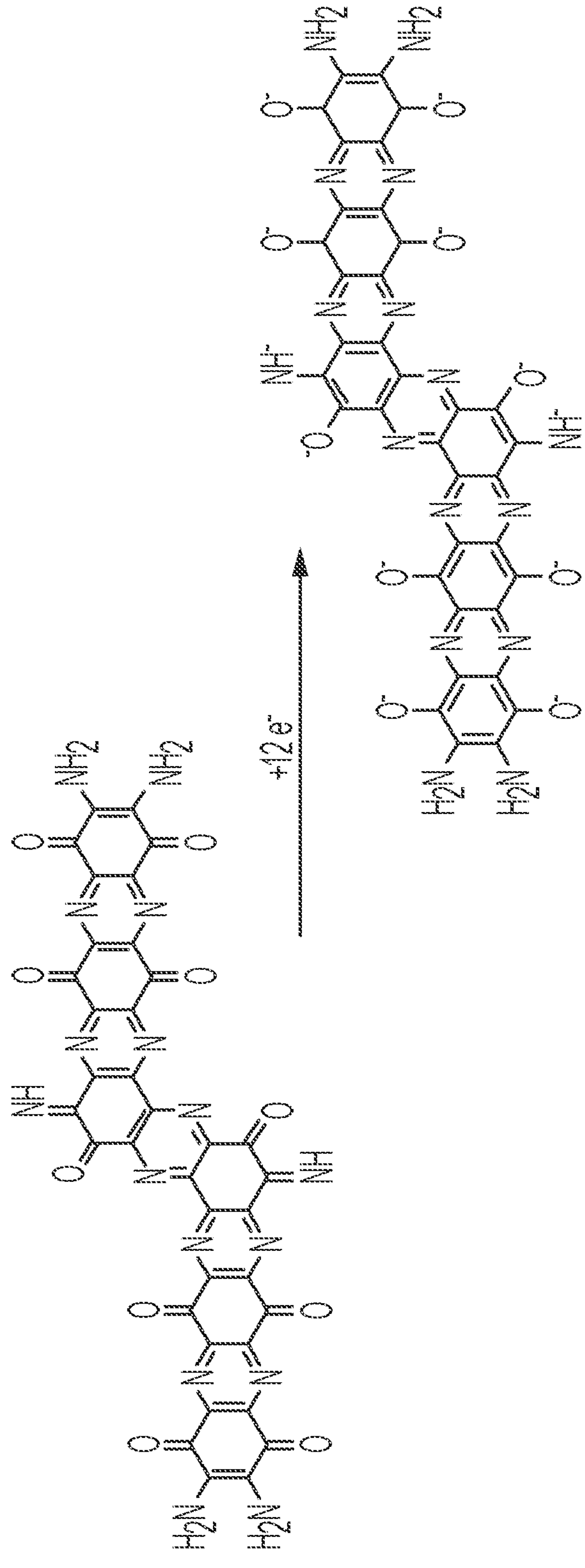
FIG. 30 shows, according to certain embodiments, a schematic representation of the 12-electron reduction of pBTABQ.

For pBTABQ, the theoretical capacity is calculated to be 389 mAh $g^{-1}$, based on the redox process shown in FIG. 30 (n=12).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or." as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of." or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of." "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B." or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition, comprising:

a bis-tetraamino-benzoquinone molecule of the structure:

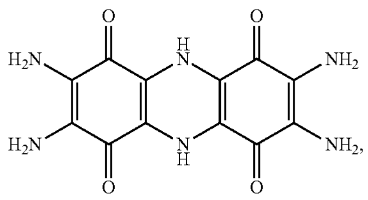 [SMILES: Nc1c(N)c(=O)c2[nH]c3c(=O)c(N)c(N)c(=O)c3[nH]c2c1=O]

and/or a tautomer, oligomer, and/or polymer thereof.

2. An electrode, comprising:

a bis-tetraamino-benzoquinone molecule of the structure:

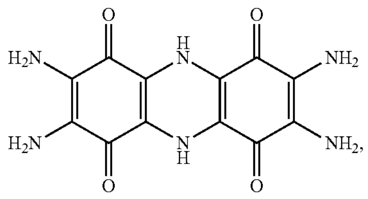 [SMILES: Nc1c(N)c(=O)c2[nH]c3c(=O)c(N)c(N)c(=O)c3[nH]c2c1=O]

and/or a tautomer, oligomer, and/or polymer thereof.

3. The electrode of claim 2, comprising a plurality of bis-tetraamino-benzoquinone molecules and/or tautomers, oligomers, and/or polymers thereof.

4. The electrode of claim 3, wherein at least a portion of the plurality of bis-tetraamino-benzoquinone molecules and/or tautomers, oligomers, and/or polymers thereof interact with each other in a planar and/or two-dimensional configuration via hydrogen-bonding.

5. The electrode of claim 3, wherein at least a portion of the plurality of bis-tetraamino-benzoquinone molecules and/or tautomers, oligomers, and/or polymers thereof interact with each other in a three-dimensional stacking configuration via π-π interactions.

6. The electrode of claim 2, wherein the electrode has an electrical conductivity greater than or equal to $10^{-7}$ S/cm.

7. The electrode of claim 2, wherein the electrode has a specific capacitance greater than or equal to 300 F/g.

8. The electrode of claim 7, wherein the specific capacitance is measured at a scan rate of 0.2 mV/s.

9. The electrode of claim 2, wherein the electrode has a cycling performance greater than or equal to 20,000 cycles.

10. The electrode of claim 9, wherein the cycling performance is measured at a scan rate of 30 mV/s.

11. An electrochemical cell, comprising:

a first electrode;

a second electrode; and an electrolyte, wherein the first electrode and/or the second electrode is an electrode of claim 2.

12. The electrochemical cell of claim 11, wherein the electrolyte comprises a liquid electrolyte solvent having a pH greater than or equal to 0 and less than or equal to 2.

13. The electrochemical cell of claim 11, wherein the electrolyte comprises a liquid electrolyte solvent having a pH greater than or equal to 12 and less than or equal to 15.

14. An electrochemically active charge storage material, comprising:

an active material comprising a fused aromatic system comprising carbon atoms, hydrogen atoms, and a plurality of heteroatoms each replacing a carbon atom, wherein:

the ratio of carbon atoms to heteroatoms is greater than 1 and less than 2, wherein the plurality of heteroatoms comprise N, O, S, and/or Se; and at least a portion of the fused aromatic system is in a planar and/or two-dimensional configuration via a number of hydrogen-bonding interactions, wherein the number of hydrogen-bonding interactions is greater than or equal to 0.3 and less than or equal to 1 hydrogen-bond per mole of carbon atoms.

15. A charge storage device, comprising:

an electrochemically active charge storage material, comprising an active material comprising a fused aromatic system comprising carbon atoms, hydrogen atoms, and a plurality of heteroatoms each replacing a carbon atom, wherein the ratio of carbon atoms to heteroatoms is greater than 1 and less than 2, and wherein the plurality of heteroatoms comprise N, O, S, and/or Se;

wherein the electrochemically active charge storage material has a charge capacity of greater than or equal to 100 mAh per gram of active material; and/or the electrochemically active charge storage material has a charge capacity of greater than or equal to 50 mAh per gram of electrochemically active charge storage material; and/or the electrochemically active charge storage material delivers at least 90% of its charge capacity at a voltage higher than 2.0 V vs. a Lit/Li standard reference electrode.

16. The charge storage device of claim 15, wherein the charge capacity is delivered at a charge and/or discharge rate that is less than 60 seconds.

17. A charge storage device, comprising:

an electrochemically active charge storage material, comprising an active material comprising a fused aromatic system comprising carbon atoms, hydrogen atoms, and a plurality of heteroatoms each replacing a carbon atom, wherein the ratio of carbon atoms to heteroatoms is greater than 1 and less than 2, and wherein the plurality of heteroatoms comprise N, O, S, and/or Se;

wherein the electrochemically active charge storage material is disposed in an electrolyte, and the electrochemically active charge storage material has a charge capacity that is at least 50% greater when a pH value of the electrolyte is greater than or equal to 0 and less than or equal to 2 or greater than or equal to 12 and less than or equal to 15 as compared to when the pH value of the electrolyte is greater than and less than 12.

18. A charge storage device, comprising:

an electrochemically active charge storage material, comprising an active material comprising a fused aromatic system comprising carbon atoms, hydrogen atoms, and a plurality of heteroatoms each replacing a carbon atom, wherein the ratio of carbon atoms to heteroatoms is greater than 1 and less than 2, and wherein the plurality of heteroatoms comprise N, O, S, and/or Se;

wherein a ratio of moles of electrons stored as charge per mole of heteroatoms is greater than or equal to 0.3 and less than or equal to 0.6.

19. A charge storage device, comprising:

an electrochemically active charge storage material, comprising an active material comprising a fused aromatic system comprising carbon atoms, hydrogen atoms, and a plurality of heteroatoms each replacing a carbon atom, wherein the ratio of carbon atoms to heteroatoms is greater than 1 and less than 2, and wherein the plurality of heteroatoms comprise N, O, S, and/or Se;

wherein the charge storage device is a capacitor or a supercapacitor.

* * * * *